US011785913B2

(12) United States Patent
Kerrigan et al.

(10) Patent No.: US 11,785,913 B2
(45) Date of Patent: Oct. 17, 2023

(54) MUSHROOM LINE J14756-S3 AND METHODS AND USES THEREFOR

(71) Applicant: SYLVAN AMERICA, INC., Kittanning, PA (US)

(72) Inventors: Richard Kerrigan, Kittanning, PA (US); Mark Wach, Allison Park, PA (US); Michelle Schultz, New Bethlehem, PA (US); Mark G. Loftus, Oakmont, PA (US); Michael A. Kessler, Kittanning, PA (US); William P. Swanik, Petrolia, PA (US); Anne Rodier, Saumur (FR); Anica Amini, Saint-Pierre-des-Corps (FR); Sylvie Delbecque, Langeais (FR); Richard Rucklidge, West Sussex (GB)

(73) Assignee: SYLVAN AMERICA, INC., Kittanning, PA (US)

( * ) Notice: Subject to any disclaimer, the term of this patent is extended or adjusted under 35 U.S.C. 154(b) by 47 days.

(21) Appl. No.: 16/465,214

(22) PCT Filed: Nov. 28, 2017

(86) PCT No.: PCT/US2017/063405
§ 371 (c)(1),
(2) Date: May 30, 2019

(87) PCT Pub. No.: WO2018/102290
PCT Pub. Date: Jun. 7, 2018

(65) Prior Publication Data
US 2020/0084993 A1    Mar. 19, 2020

Related U.S. Application Data

(60) Provisional application No. 62/428,597, filed on Dec. 1, 2016.

(51) Int. Cl.
*A01H 15/00* (2006.01)
*C12N 1/14* (2006.01)
*A01G 18/00* (2018.01)

(52) U.S. Cl.
CPC .............. *A01H 15/00* (2013.01); *A01G 18/00* (2018.02); *C12N 1/14* (2013.01); *C12N 1/145* (2021.05)

(58) Field of Classification Search
CPC .................................. A01G 18/00; C12N 1/145
See application file for complete search history.

(56) References Cited

U.S. PATENT DOCUMENTS

| 7,608,760 B2 | 10/2009 | Robles et al. |
| 8,663,969 B2 | 3/2014 | Kerrigan et al. |
| 9,017,988 B1* | 4/2015 | Kerrigan ................ C12N 1/145 435/254.1 |
| 9,622,428 B2 | 4/2017 | Kerrigan et al. |
| 9,642,333 B2 | 5/2017 | Kerrigan et al. |
| 10,051,831 B2 | 8/2018 | Kerrigan et al. |
| 2010/0212042 A1 | 8/2010 | Robles et al. |

OTHER PUBLICATIONS

Micheline Imbernon, et al.; MYCOLOGIA; 88(5), 1996, pp. 749-761; BSN, the Primary Determinant of basidial spore number and reproductive mode in Agaricus bisporus, maps to chromosome I; 13 pages.
Emmanuelle Morin, et al.; Environmental Sciences; www.pnas.org; 4146-4148, PNAS, Mar. 5, 2013, vol. 110, No. 10; 9 pages.
Richard W. Kerrigan, et al.; Meiotic Behavior and Linkage Relationships in the Secondarily Homothallic Fungus Agaricus Bisporus; Publication Oct. 14, 1992; 12 pages.
A.J. Velcko, Jr. et al.; Expression of Novel Genes in Agaricus Bisporus Using an Agrobacterium-mediated Transformation Technique; 4 pages.
D.M. Beyer; Department of Plant Pathology, The Pennsylvania State University. Plant Disease—97 (1):142—Abstract; apsjournais.apsnet.org/doi/abs/10.1094/PDIS-07-12-0619-PDN; Jan. 2013, vol. 97, No. 1p. 142; 2 pages.
Callac, P., et a., 1998. Evidence for PPC1, a determinant of the pilei-pellis color of Agaricus bisporus fruitbodies. Fungal Genet. Biol. 23, 181-188.
Foulongne-Oriol, et ai., 2010. An expanded genetic linkage map of an intervarietal *Agaricus bisporus* var. bisporus—*A. bisporus* var. burnettii hybrid based on AFLP, SSR and CAPS markers sheds light on the recombination behaviour of the species. Fungal Genetics and Biology 47: 226-236.
Kerrigan, R.W., et al., 1993.Meiotic behavior and linkage relationships in the secondarily homothallic fungus Agaricus bisporus. Genetics 133, 225-236.
Loftus, M., et al., 2000. Use of SCAR marker for cap color in Agaricus bisporus breeding programs. Mush. Sci. 15, 201-205.
Morin, et al., 2012. Genome sequence of the button mushroomAgaricus bisporus reveals mechanisms governing adaptation to a humic-rich ecological niche. Proc Natl Acad Sci USA 109: 17501-17506.
Schoch, Conrad L., et al., 2012. Nuclear ribosomal internal transcribed spacer (ITS) region as a universal DNA barcode marker for Fungi. Proc. Nat. Acad. Sci. <www.pnas.org/cgi/content/short/1117018109>.
Xu, J.-P., et al. 1993, Localization of the mating type gene in Agaricus bisporus. App. Env. Microbiol. 59(9):3044-3049.

* cited by examiner

*Primary Examiner* — David H Kruse
(74) *Attorney, Agent, or Firm* — Renner, Kenner, Greive, Bobak Taylor & Weber

(57) ABSTRACT

A mushroom culture of *Agaricus bisporus*, comprising at least one set of chromosomes as a culture of line J14756-s3, includes a representative culture of the line, which has been deposited under NRRL Accession No. 67317. A method of producing a hybrid mushroom culture of *Agaricus bisporus* comprising: mating a culture comprising at least one set of chromosomes as a culture of line J14756-s3 with a second homokaryotic line culture. Additionally, mushrooms, parts of the culture and products incorporating the culture of the invention are provided.

27 Claims, No Drawings
Specification includes a Sequence Listing.

MUSHROOM LINE J14756-S3 AND METHODS AND USES THEREFOR

CROSS-REFERENCE TO RELATED APPLICATIONS

This application is a 371 national phase filing from PCT Application No. PCT/US2017/063405, filed Nov. 28, 2017, which claims the benefit of U.S. Provisional Application No. 62/428,597, filed Dec. 1, 2016.

TECHNICAL FIELD

This invention relates generally to the field of microorganism strain development and more particularly, to the development of a homokaryotic line of mushroom fungus. More specifically, the present invention relates to the development of a homokaryotic *Agaricus bisporus* mushroom fungus line culture designated J14756-s3 and to cultures descended, or otherwise derived, from line J14756-s3. The present invention further relates to F1 hybrids, and to a particular F1 hybrid strain, designated J15051, descended from J14756-s3. The invention additionally relates to lines and strains derived from or descended from, or otherwise developed from, line J14756-s3 and F1 hybrids incorporating line J14756-s3 including strain J15051. The invention further relates to methods of use of the cultures described hereinabove.

BACKGROUND OF THE INVENTION

The edible mushroom *Agaricus bisporus* (Lange) Imbach var. *bisporus*, a microorganism belonging to the basidiomycete fungi, is widely cultivated around the world. Accordingly, development of novel hybrid mushroom strains or lines of this mushroom fungus is seen as highly desirable to the cultivated mushroom industry, particularly if those novel strains or lines can be developed to provide various desirable traits within a single strain, culture, hybrid or line.

Cultures are the means by which the mushroom strain developers prepare, maintain, and propagate their industrial microorganisms. Cultures of *Agaricus*, like those of other microorganisms, are prepared, maintained, propagated and stored on sterile media using various microbiological laboratory methods and techniques known in the art. Sterile tools and aseptic techniques are used within clean rooms or sterile transfer hoods to manipulate cells of pure cultures for various purposes including clonal propagation and for the development of new strains using diverse techniques. Commercial culture inocula including mushroom 'spawn' and 'casing inoculum' are also prepared using large-scale microbiological production methods, and are provided to the end user as pure cultures contained within sterile packaging.

One use of such cultures is to produce mushrooms. Mushrooms are cultivated commercially within purpose-built structures on dedicated farms. While there are many variations on methods, and no single standard cultivation method, the following description represents a typical method. Compost prepared from lignocellulosic material such as straw, augmented with nitrogenous material, is finished and pasteurized within a suitable facility. Mushroom spawn, which comprises a sterilized friable 'carrier substrate' onto which a pure culture of one mushroom strain has been aseptically incorporated via inoculum and then propagated, is mixed with the pasteurized compost and is incubated for approximately 13 to about 19 days at a controlled temperature, during which time the mycelium of the mushroom culture colonizes the entire mass of compost and begins to digest it. A non-nutritive 'casing layer' of material such as peat is then placed over the compost to a depth of from about 1.5 to about 2 inches. Additional 'casing inoculum' incorporating the same mushroom culture may be incorporated into the casing layer to accelerate the formation and harvesting of mushrooms, and improve uniformity of the distribution of mycelium and mushrooms in the casing and on the casing surface. Environmental conditions, including temperature and humidity, in the commercial cropping facility are then carefully managed to promote and control the transition of the culture from vegetative to reproductive growth at the casing/air interface. In a further about 13 to about 18 days after casing, mushrooms will have developed to the correct stage for harvest and sale. Earlier harvest timing accelerates cash flow, compresses the production cycle in the facility which allows for more production cycles per year, and provides for a greater proportion of the crop to be harvested before the incidence of disease increases and compromises a relatively greater fraction of the crop, which is a routine problem. A flush (or "break") of mushrooms comprising the original culture will be picked over a 3 to 4 day period. Additional flushes of mushrooms appear at about weekly intervals. Commercially, two or three flushes of mushrooms are produced and harvested before the compost is removed and replaced in the cropping facility. Harvested mushrooms are then graded, sorted, weighed, packed and shipped under refrigeration. Profitability associated with a strain is dependent upon (1) the yield weight of the harvested crop, net of losses from disease, damage and post-harvest weight loss, (2) variable costs of harvesting or processing mushrooms of different sizes, weights, spacing/timing behaviors, and types or grades, and (3) the quality and marketability of the mushroom product as determined by appearance, physical characteristics, shelf life, and market segment (for example white-capped vs. brown-capped, or closed-capped vs. open-capped) of the product.

*Agaricus bisporus* has a reproductive syndrome known as amphithallism, in which two distinct life cycles, namely heteromixis and intramixis, operate concurrently. As in other fungi, the reproductive propagule is a spore. *Agaricus* produces spores meiotically, on a meiosporangium known as a basidium. In a first life cycle, *A. bisporus* spores each receive a single haploid postmeiotic nucleus; these spores are competent to mate but not competent to produce mushrooms. These haploid spores germinate to produce homokaryotic offspring or lines which can mate with other sexually compatible homokaryons to produce novel hybrid heterokaryons that are competent to produce mushrooms. Heterokaryons generally exhibit much less ability to mate than do homokaryons. This lifecycle is called heteromixis, or more commonly, outbreeding. This life cycle, which is carried out to obtain new hybrid strains in strain development programs, operates but typically does not predominate in strains of *Agaricus bisporus* var. *bisporus*.

A second, inbreeding life cycle called intramixis predominates in most strains of *Agaricus bisporus* var. *bisporus*. Most spores, typically 90%-99.9%, receive two post-meiotic nuclei, and most such pairs of nuclei, typically at least 90%, consist of Non-Sister Nuclear Pairs (NSNPs) which have a heteroallelic genotype at most or all centromeric-linked loci including the MAT (=mating type) locus. That MAT genotype determines the heterokaryotic (as opposed to homokaryotic) phenotype of these offspring, which are reproductively competent and can produce a crop of mushrooms. Unusually among eukaryotes, relatively little chromosomal crossing-over is observed to have occurred in postmeiotic offspring of *Agaricus bisporus*; empirically, very little heteroallelism (analogous to heterozygosity) is lost among heterokaryotic offspring of a heterokaryotic strain. Consequently, parental and offspring heterokaryotic genotypes and phenotypes tend to closely resemble each other, as noted above. For this reason, essential derivation, e.g., the production of Essentially Derived Varieties (EDVs), is a familiar strain development technique among commercial mushroom spawn producers. It is further well understood in the art that any strain development method incorporates at least one step of selecting among the resulting strains, whether hybrids or EDVs, to obtain one or more strains which are most advantageous.

Another phenomenon exhibited by *Agaricus bisporus* and other basidiomycete fungi is vegetative incompatibility. Empirically, it is regularly observed that, in physical contact, a first strain is unable to fuse (anastomose) freely and grow together with any other genetically distinct strain, in other words, with any other strain having less than complete genetic identity with a first strain. The genetics are only partially understood for 'model' basidiomycetes, but are known to involve multiple genes and alleles, providing such a large number of combinations that, for practical purposes, each genotype (and each independent strain, including wild strains, cultivars, and hybrids) is extremely unlikely to reoccur in a second strain, and therefore, is effectively unique. The vegetative incompatibility phenotype has two significant commercial and technical implications. First, by using protocols that pair two strains in cropping tests, it provides a practical test of identity or non-identity between pairs of strains, independent of 'genetic fingerprinting'. Second, vegetative incompatibility between non-identical strains retards or even prevents the transmission of detrimental viruses between different strains.

There is a need for more diverse, more versatile, and more profitable *Agaricus bisporus* mushroom strains. To meet this need for improved *Agaricus bisporus* mushroom strains, various entities within the mushroom industry, including Sylvan America, Inc., have set up mushroom strain development programs. The goal of a mushroom strain development program is to combine, in a single strain, culture, hybrid, or line, various desirable traits. Strains currently available to the mushroom industry allow growers to produce crops of mushrooms successfully and profitably. There are many characteristics by which a novel strain might be judged as improved over existing strains, or more suitable, in a particular production facility or sales market, or in the industry regionally or globally. Such characteristics can be assessed using techniques that are well known in the art. In reality, practically speaking, some valuable characteristics become evident only over time as different growing techniques are evaluated under multiple sets of conditions, including novel conditions that may arise unpredictably. Novel strains are most preferably and successfully developed from new hybridizations between haploid homokaryotic lines, including novel lines. Thus, the need continues to exist for new lines that can be used to produce new hybrid strains of *Agaricus bisporus* mushroom cultures and microorganisms that in turn provide improved and/or novel combinations of characteristics for producer profitability and for improved mushroom products over other previous strains of *Agaricus bisporus*.

In Applicant's aggregate operating experience of almost 100 years of mushroom strain development in Applicant's breeding centers, it has been extremely difficult to develop more than a handful of strains which are acceptable with respect to all necessary commercial characteristics. Successful outcomes are rare and generally unpredictable, and rely in part on the serendipitous identification of breeding stocks and lines that are discovered to demonstrate an ability to produce one or more commercially acceptable strains via application of strain development techniques. While many traits could cause a strain not to be commercially acceptable, three of the foremost qualifying traits are crop yield, crop timing, and appearance/"quality" of the mushrooms produced. Therefore, any novel breeding stock or line with the ability to produce acceptable new commercial strains via the application of strain development techniques is of great value to the mushroom strain developer and to the mushroom industry.

Market conditions change over time. Consumer preferences shift and evolve. New pathogens emerge. Therefore, spawn producers and mushroom producers need access to commercially acceptable strains that present different, alternative combinations of characters that allow for flexible and effective responses to changing market or production conditions, including challenges which may be unforeseeable. Genetic diversity is responsible for diversity of phenotypic characters including both evident characteristics and others which might not become evident or explicitly valuable except under changed or unpredictable conditions.

Thus, there is a general need for commercially acceptable *A. bisporus* strains with different, diverse, novel genotypes, relative to other commercially produced strains, for three reasons. First, strains vegetatively incompatible with other strains in commercial production are known to retard the spread of viral diseases between cultivated strains, due to an inability, or limited ability, of incompatible strains to anastomose (=physically fuse) with each other and exchange cytoplasm. The incompatibility phenotype can be assessed using techniques that are well known in the art. Alternating or rotating the use of incompatible strains within a facility can improve harvest yields immediately, by sharply reducing the transmission/infection rate, while reducing viral disease reservoirs and pressure over a period of weeks or months.

Second, it is well understood that when an agricultural crop industry relies extensively on a single genetic lineage (i.e., creates a commercial monoculture as now exists in most countries for white-capped mushrooms, which are all part of the commercially dominant U1 lineage of *A. bisporus*), there is an increased risk of unpredictable, catastrophic crop failure on a facility-wide or even industry-wide scale, due to emerging diseases or other conditions. In the year 2016, only three unique genotypic lineages are in wide commercial use in North America, and only two are in wide use in Europe. Therefore from a risk management and food security perspective, it is highly desirable to simultaneously provide both genetic diversification and commercially acceptable performance and crop characteristics in an expanded range of commercially available strains.

Third, it is understood that flavor ("taste") is perceived by different persons in highly individual ways. Both untrained and trained tasters register idiosyncratic preferences for mushrooms produced by different strains; there is no single "best-tasting" mushroom strain, but rather a diverse collection of individual preferences. Providing genetically diverse offerings of mushrooms provides the consumer with more options and a better chance of finding a mushroom that may become a personal "flavor favorite". Increased consumer satisfaction supports increased sales pricing and volume and is beneficial to all parties.

Thus, any commercially acceptable hybrid strain, or breeding line, with a novel genotype is useful and advantageous in overcoming the industry-scale problem of limited genetic diversity and crop resilience, and also the problem of limited options for crop rotation and facility hygiene management, while increasing the prospects for broader consumer acceptance and satisfaction. The use of novel lines that incorporate DNA from non-cultivar stocks meets the need of providing important genetic diversification of the strain pool used to produce crops of cultivated *A. bisporus* mushrooms. There is an even greater need for diverse and novel breeding lines capable of being used to produce diverse, novel commercially acceptable hybrid strains via strain development techniques. There is a correspondingly great need for the novel hybrid strains so produced in such usage.

There is also a need for commercially acceptable mushroom strains that are genetically distinct and, therefore, vegetatively incompatible with other commercial strains now in use, for example with one or more of six brown-capped strain lineages known or used in the art: The "Old Fashioned Brown" including SB-65, SB-295, and 2400; S-600/X618; BR06/"Heirloom", B14528/"Tuscan"; "Broncoh", and J10263/"Forestiere" strain lineages.

The mushroom industry has need of strains that (1) produce an acceptable yield of mushrooms, for example a yield of at least 95% of current commercial strains such as BR06/"Heirloom" or B14528/"Tuscan", (2) on a typical commercial production schedule, in other words on the same harvest schedule as another commercial brown-capped strain, particularly strains in the group including Old Fashioned Brown strains including SB-65, SB-295, and 2400; S-600/X618; BR06/"Heirloom", B14528/"Tuscan"; "Broncoh" and J10263/"Forestiere", or on an even faster schedule, while also producing mushrooms of good appearance and high quality for the consumer. There is a further need for new strains that meet the above criteria while (3) also producing mushrooms with a "medium-brown" cap color that is a lighter color than that of mushrooms produced by at least one strain in the group selected from: BR06/"Heirloom", B14528/"Tuscan".

Beginning around 2008, hybrid mushroom strains with dark brown caps and good productivity became available commercially. Since that time, consumer preferences in some market segments have shifted to accept the darker brown cap color. However, based on overall experience, other market segments have been more resistant to the dark brown cap color of these mushroom products and desire a medium-brown mushroom. Additionally, some retailers desire to display for customers the broadest selection of visually distinct produce types in each category of produce, and would prefer to offer "medium-brown"-capped mushrooms for sale side-by-side with very dark mushrooms.

Therefore, there is a need for mushroom strains which produce crops of mushrooms having a medium-brown cap color that can be distinguished, as being lighter in color, from dark-brown-capped mushroom strains, while also having commercially acceptable characteristics such as timing, yield, and 'quality'. There is a corresponding need for mushroom lines that can transmit genetic material capable of providing these traits in their hybrid descendent strains.

Therefore, the need exists for the development of new *Agaricus bisporus* strains, and for new breeding lines that can be used to produce new strains, that meet the needs and desires of mushroom producers, marketers and consumers.

SUMMARY OF THE INVENTION

The present invention is directed generally to at least a new and distinct homokaryotic line of *Agaricus bisporus* designated J14756-s3, and to lines having genetic, clonal, physiological and morphological identity with J14756-s3, to processes for using the line designated, or identical with, J14756-s3, including the development of novel hybrid cultures of strains and lines belonging to a genealogical pedigree formed from the initial culture of strain J14756, to those cultures, and their parts, of lines and strains descended from J14756-s3, and to the uses of those cultures of novel hybrid strains and lines developed from and genealogically descended or derived from J14756-s3. A deposit of a culture of the *Agaricus bisporus* line J14756-s3, as disclosed herein, has been made by Sylvan, Inc. d/b/a Sylvan Biosciences, 198 Nolte Dr., Kittanning, Pa. 16201 USA, with the Agricultural Research Services Culture Collection (NRRL) 1815 North University Street, Peoria, Ill. 61604 USA. The date of deposit was Sep. 18, 2016. The culture deposited was taken from the same culture maintained by Sylvan America, Inc., Kittanning, Pa., USA, the assignee, since prior to the filing date of this application, and the inventors and assignee have received authorization to refer to this deposited biological material in any and all patent applications. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 67317. The deposit will be maintained in the depository for a period of 30 years, or 5 years after the last request, or for the effective life of the patent, whichever is longer, and will be replaced as necessary during that period. The culture will be irrevocably and without restriction or condition released to the public upon the filing of the patent application or upon the issuance of a patent, whichever is required by the applicable patent laws. Line J14756-s3 has been found to have an advantageous genotype for mating to produce commercially useful hybrid strains, an attribute that was determined empirically after the fact, but which could not be predicted successfully using any existing known method.

In one or more embodiments, the invention comprises a culture of the line J14756-s3, and lines and cells having genetic, clonal, physiological and morphological identity with J14756-s3, in other words, lines and cells which are indistinguishable from line J14756-s3.

In one embodiment, the invention is directed to a culture comprising at least one set of chromosomes of an *Agaricus bisporus* line J14756-s3, the culture of the line J14756-s3 having been deposited under the NRRL Accession Number 67317, wherein said chromosomes comprise all of the alleles reported for the line J14756-s3 at the sequence-characterized marker loci listed in at least one of Tables I and II. In another embodiment, the culture is an *Agaricus bisporus* culture having all of the physiological and morphological characteristics of line J14756-s3, wherein the culture of said line J14756-s3 was deposited under the NRRL Accession Number 67317.

In another embodiment, the culture comprising at least one set of chromosomes of an *Agaricus bisporus* line J14756-s3 is an F1 hybrid *Agaricus bisporus* mushroom culture. In another embodiment, the culture comprising at least one set of chromosomes of an *Agaricus bisporus* line J14756-s3 is an F1 hybrid *Agaricus bisporus* mushroom culture produced by mating a culture of the line J14756-s3 with a different *Agaricus bisporus* culture. In another embodiment, the culture comprising at least one set of chromosomes of an *Agaricus bisporus* line J14756-s3 is an F1 hybrid *Agaricus bisporus* mushroom culture having line J14756-s3 and a different *Agaricus bisporus* culture as direct parents. Thus, it will be appreciated that one or more method for the production of an F1 hybrid *Agaricus bisporus* mushroom culture comprises the step of mating a culture of the line J14756-s3 with a second, different *Agaricus bisporus* culture.

In another embodiment, the resultant F1 hybrid *Agaricus bisporus* mushroom culture may be a culture of strain J15051, the culture of strain J15051 having been deposited under the NRRL accession number 67316. The deposit of a culture of the *Agaricus bisporus* strain J15051, as disclosed herein, has been made by Sylvan Inc. d/b/a Sylvan Biosciences, 198 Nolte Dr., Kittanning, Pa. 16201 USA, with the Agricultural Research Services Culture Collection (NRRL) 1815 North University Street, Peoria, Ill. 61604 USA. The date of deposit was Sep. 18, 2016. The culture deposited was taken from the same culture maintained by Sylvan America, Inc., Kittanning, Pa., USA, the assignee, since prior to the filing date of this application, and the inventors and assignee have received authorization to refer to this deposited biological material in any and all patent applications. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 67316. The deposit will be maintained in the depository for a period of 30 years, or 5 years after the last request, or for the effective life of the patent, whichever is longer, and will be replaced as necessary during that period. The culture will be irrevocably and without restriction or condition released to the public upon the filing of the patent application or upon the issuance of a patent, whichever is required by the applicable patent laws.

In some embodiments, the culture may be obtained using at least one strain development technique selected from the group consisting of inbreeding, including intramixis, outbreeding, i.e., heteromixis, selfing, backcrossing, introgressive trait conversion, essential derivation, somatic selection, single-spore selection, multispore selection, pedigree-assisted breeding, marker assisted selection, mutagenesis and transformation, and applying said at least one strain development technique to a first mushroom culture, or parts thereof, said first culture comprising at least one set of chromosomes of an *Agaricus bisporus* line J14756-s3.

In other embodiments, the culture is a culture derived, descended, or otherwise obtained from an initial culture of the invention, comprising at least one set of chromosomes of *Agaricus bisporus* line J14756-s3, thus having at least one genealogical relationship with the initial culture, wherein that genealogical relationship is selected from the group consisting of (1) identity: self, clone, and (2) descent: inbred descendent, outcrossed descendent, backcrossed descendent, F1 hybrid, F2 hybrid, F3 hybrid, F4 hybrid, F5 hybrid, and Essentially Derived Variety.

In other embodiments the Essentially Derived Variety may have, as the initial culture from which it is derived, one of the following cultures: an *Agaricus bisporus* haploid line culture J14756-s3, a haploid line culture comprising at least one set of chromosomes of an *Agaricus bisporus* line J14756-s3, a hybrid heterokaryotic culture obtained by mating J14756-s3 with a second culture to produce an F1 generation, any culture of generation F2, F3, F4, F5, inclusive, that is obtained from the F1 generation of the invention, a culture obtained from line J14756-s3 by using at least one strain development technique, an inbred descendent of J14756-s3, an outcrossed descendent of J14756-s3, and an EDV of any culture that was obtained from J14756-s3 by using at least one strain development technique. In one or more of these embodiments, the Essentially Derived Variety culture has at least 75% genotypic and genomic identity with the culture of line J14756-s3. In one or more of these embodiments, the Essentially Derived Variety culture has at least 75% genotypic and genomic identity with the culture of the F1 hybrid produced by mating line J14756-s3 with a second, different *Agaricus bisporus* culture. In one or more of these embodiments, the Essentially Derived Variety culture has at least 75% genotypic and genomic identity with the culture of strain J15051.

In another embodiment, the F1 hybrid culture obtained by mating line J14756-s3 with a second *Agaricus bisporus* line produces, when grown under the same commercial conditions with at least one dark-brown strain selected from the group consisting of BR06/"Heirloom" and B14528/"Tuscan", a crop of mushrooms (1) having a cap color that is a lighter brown color than that of mushrooms produced by at least one of the dark-brown strains selected from said group, and wherein (2) the crop is produced not later than crops produced by at least one of the dark-brown strains selected from the group, and wherein (3) the crop yield is at least 95% of the yield of at least one of the dark-brown strains selected from the group.

In another embodiment, the F1 hybrid culture obtained by mating line J14756-s3 with a second *Agaricus bisporus* line has a representation of genetic identity, such as a multilocus genotype, genetic fingerprint, or genome sequence, that is genetically distinct from, i.e., having not more than 99% genetic identity with, that of all strains selected from the group consisting of Old Fashioned Brown strains, SB-65, SB-295, 2400, S-600/X618, BR06/"Heirloom", B14528/"Tuscan", Broncoh, and J10263/"Forestiere". In another embodiment, the F1 hybrid culture obtained by mating line J14756-s3 with a second *Agaricus bisporus* line is vegetatively incompatible with all strains selected from the group consisting of Old Fashioned Brown strains, SB-65, SB-295, 2400, S-600/X618, BR06/"Heirloom", B14528/"Tuscan", Broncoh, and J10263/"Forestiere". Further embodiments are parts of a culture of the invention including hyphae, mushrooms, spores, cells, nuclei and mitochondria. Further embodiments are products, including mycelium, spawn, inoculum, casing inoculum, fresh mushrooms, processed mushrooms, mushroom pieces, and colonized substrates including grain, compost, and friable particulate matter, that comprise a culture of the invention. Thus, it is yet another embodiment of the present invention to provide a product comprising a mushroom culture having at least one genealogical relationship with the culture of claim 1, selected from the group of genealogical relationships consisting of: (1) identity: self, clone, and (2) descent: inbred descendent, outcrossed descendent, backcrossed descendent, F1 hybrid, F2 hybrid, F3 hybrid, F4 hybrid, F5 hybrid, Essentially Derived Variety, wherein the product is selected from the group consisting of mycelium, spawn, inoculum, casing inoculum, fresh mushrooms, processed mushrooms, mushroom pieces, and colonized substrates including grain, compost, and friable particulate matter. An embodiment of the present invention may further include a mushroom produced by growing a crop of mushrooms from a culture having at least one genealogical relationship, to the mushroom culture of claim 1, selected from the group consisting of self, clone, inbred descendent, outcrossed descendent, backcrossed descendent, F1 hybrid, F2 hybrid, F3 hybrid, F4 hybrid, F5 hybrid, and Essentially Derived Variety.

A further embodiment of the invention is a method for developing a resultant culture in a mushroom strain development program comprising: applying at least one mushroom strain development technique to a first mushroom culture, or parts thereof, wherein said first mushroom culture is a culture selected from the group comprising: a culture of line J14756-s3, a culture having all of the physiological and morphological characteristics of line J14756-s3, a culture comprising at least one set of chromosomes of *Agaricus bisporus* line J14756-s3, wherein said chromosomes comprise all of the alleles reported for the line J14756-s3 at the sequence-characterized marker loci listed in at least one of Table I and Table II, wherein the culture of said line J14756-s3 was deposited under the NRRL Accession Number 67317, to provide the second resultant culture. The mushroom strain development techniques may be selected from the group consisting of inbreeding, outbreeding, selfing, backcrossing, introgressive trait conversion, essential derivation, somatic selection, single-spore selection, multi-spore selection, pedigree-assisted breeding, marker assisted selection, mutagenesis and transformation.

Another embodiment of this invention is a process of producing a hybrid mushroom culture, comprising: physically mating a first *Agaricus bisporus* mushroom culture with a second *Agaricus bisporus* mushroom culture (a second parental culture), wherein at least one of the first and second *Agaricus bisporus* mushroom cultures is a culture having all of the physiological and morphological characteristics of line J14756-s3, wherein the culture of said line J14756-s3 was deposited under the NRRL Accession Number 67317. Another embodiment is a process for introducing a desired trait into a culture of *Agaricus bisporus* line J14756-s3 comprising the steps of: (a) physically mating the culture of *Agaricus bisporus* line J14756-s3 to a second resultant culture of *Agaricus bisporus* having the desired trait, to produce a hybrid; (b) obtaining an offspring of the hybrid that carries at least one gene that determines the desired trait from the hybrid; (c) mating said offspring of the hybrid with the culture of *Agaricus bisporus* line J14756-s3 to produce a new hybrid; (d) repeating steps (b) and (c) at least once to produce a subsequent hybrid; (e) obtaining a homokaryotic line carrying at least one gene that determines the desired trait and comprising at least 75% of the alleles of line J14756-s3, at sequence-characterized marker loci described in one of Tables I and II, from the subsequent hybrid of step (d). Another embodiment is a method of producing a mushroom culture comprising the steps of: (a) growing a progeny culture produced by mating the culture of claim 1 with a second *Agaricus bisporus* culture; (b) mating the progeny culture with a different culture or with itself via at least one offspring line to produce a progeny culture of a subsequent generation; (c) growing a progeny culture of a subsequent generation and mating the progeny culture of a subsequent generation with itself or a different culture; and (d) repeating steps (b) and (c) for an additional 0-5 generations to produce a mushroom culture. A further embodiment is a method of mushroom strain development comprising the steps of: (a) obtaining a molecular marker profile of *Agaricus bisporus* mushroom line J14756-s3, a culture of said line having been deposited under the NRRL Accession Number 67317; (b) obtaining an $F_n$ hybrid culture for which a mushroom culture comprising at least one set of chromosomes of *Agaricus bisporus* line J14756-s3 is a parent, wherein n is an integer 1 to 10; (c) mating a culture obtained from the $F_n$ hybrid culture with a different mushroom culture to produce an $F_{(n+1)}$ hybrid culture; and (d) selecting progeny of the $F_{(n+1)}$ hybrid culture that possess characteristics of said molecular marker profile of line J14756-s3.

Further embodiments that are obtained from these strain development processes include a hybrid culture, a part of the hybrid culture, a mushroom and its pieces and parts obtained by growing a crop from the hybrid culture, and a product incorporating the hybrid culture, said product being selected from the group consisting of mycelium, spawn, inoculum, casing inoculum, fresh mushrooms, processed mushrooms and mushroom pieces, colonized substrates, grain, compost, and friable particulate matter. Further embodiments include novel lines, strains, genealogical descendents and Essentially Derived Varieties, obtained from an initial culture of the invention by using any of the strain development processes described herein. Other embodiments include a culture that has a genome comprising a single locus trait conversion of the genome of line J14756-s3 obtained by using those same strain development processes. Further embodiments include a culture in which the single locus of the single locus trait conversion of the genome of J14756-s3 confers a trait selected from the group consisting of mushroom size, mushroom shape, mushroom cap roundness, mushroom flesh thickness, mushroom color, mushroom surface texture, mushroom cap smoothness, mushroom flavor, tissue density, tissue firmness, delayed maturation, basidial spore number greater than two, sporelessness, increased dry matter content, increased shelf life, reduced bruising, increased yield, altered distribution of yield over time, decreased spawn to pick interval, resistance to infection by symptoms of or transmission of bacterial, viral or fungal disease or diseases, insect resistance, nematode resistance, ease of crop management, suitability of crop from mechanical harvesting, desired behavioral response to environmental conditions, to stressors, to nutrient substrate composition, to seasonal influences, and to farming practices.

Various objects, features, aspects, and advantages of the present invention will become more apparent from the following detailed description of preferred embodiments of the invention.

DETAILED DESCRIPTION OF THE INVENTION

Initially, in order to provide clear and consistent understanding of the specification and claims, including the scope to be given such terms, the following definitions are provided.

Allele: one of two or more alternative forms of a gene that arise by mutation and are found at the same place on a chromosome; a heritable unit of the genome at a defined locus, ultimately identified by its DNA sequence (or by other means).

Amphithallism: A reproductive syndrome in which heteromixis and intramixis are both active.

Anastomosis: Fusion of two or more hyphae that achieves cytoplasmic continuity.

Basidiomycete: A monophyletic group of fungi producing meiospores on basidia; a member of a corresponding subdivision of Fungi such as the Basidiomycetales or Basidiomycotina.

Basidium: The meiosporangial cell, in which karyogamy and meiosis occur, and upon which the basidiospores are formed.

Bioefficiency: For mushroom crops, the net fresh weight of the harvested crop divided by the dry weight of the compost substrate at the time of spawning, for any given sampled crop area or compost weight.

Breeding: Development of strains, lines or varieties using methods that emphasize sexual mating.

Cap: Pileus; part of the mushroom, the gill-bearing structure.

Cap Roundness: Strictly, a ratio of the maximum distance between the uppermost and lowermost parts of the cap, divided by the maximum distance across the cap, measured on a longitudinally bisected mushroom; typically averaged over many specimens; subjectively, a 'rounded' property of the shape of the cap.

Carrier substrate: A medium having both nutritional and physical properties suitable for achieving both growth and dispersal of a culture; examples are substrates that are formulated for mushroom spawn, casing inoculum, and other inoculum.

Casing layer, casing: A layer of non-nutritive material such as peat or soil that is applied to the upper surface of a mass of colonized compost in order to permit development of the mushroom crop.

Casing inoculum (CI): A formulation of inoculum material incorporating a mushroom culture, typically of a defined heterokaryotic strain, suitable for mixing into the casing layer.

Cloning: Somatic propagation without selection.

Combining ability: The capacity of an individual to transmit superior performance to its offspring. General combining ability is an average performance of an individual in a particular series of matings. Compatibility: See heterokaryon compatibility, vegetative compatibility, sexual compatibility; incompatibility is the opposite of compatibility.

Culture: The tangible living organism; the organism propagated on various growth media and substrates; a portion of, or the entirety of, one physical strain, line, homokaryon or heterokaryon; the sum of all of the parts of the culture, including hyphae, mushrooms, spores, cells, protoplasts, nuclei, mitochondria, cytoplasm, DNA, RNA, and proteins, cell membranes and cell walls.

Derivation: Development from a strain; see Essentially Derived Variety (EDV).

Derived lineage group: The set of EDVs derived from a single initial strain or variety.

Descent: Genealogical descent over a limited number (e.g., 10 or fewer) of generations.

Diploid: Having two haploid chromosomal complements within a single nuclear envelope.

Directed mutagenesis: a process of altering the DNA sequence of at least one specific gene locus.

Essential derivation: A process by which an Essentially Derived Variety is obtained from an initial variety or strain or from an EDV of an initial variety or strain; modification of an initial culture using methods including somatic selection, tissue culture selection, selfing including intramictic reproduction via single spores and multiple spores and mating of sibling offspring lines, back-mating to the initial variety, or mutagenesis and/or genetic transformation of the initial variety to produce a distinct culture in which the genotype of the resulting culture is predominantly that of the initial culture.

Essentially Derived Variety (EDV): A congruent, brief, practical definition of an EDV is "a culture derived from an initial culture such that the resulting culture has present at least 75% of the genome or genotype of the initial culture". (Supplemental to the definition of an EDV, it is illustrative to note here that an EDV culture having most or all, but at least 75%, of its genome or genotype present in the genome or genotype of an initial strain or culture may be derived from an initial strain or culture by using a method selected from a group of methods comprising: (a) somatic selection, (b) tissue culture selection, selfing including (c) mating of sibling offspring lines and (d) intramictic reproduction via single or multiple spores, (e) repeated back-mating to the initial line, strain or culture, (f) mutagenesis including induced, directed and targeted mutagenesis, (g) genetic transformation, (h) a process of single-locus trait conversion, (i) a process of deheretokaryotization, (j) isolation of spontaneous mutants, to produce a culture of an EDV of an initial culture.

Flesh Thickness: A ratio of the maximum distance between the top of the stem and the uppermost part of the cap, divided by the maximum distance across the cap, measured on a longitudinally bisected mushroom; typically averaged over many specimens; subjectively called 'meatiness'.

Flush: A period of mushroom production within a cropping cycle, separated by intervals of non-production; the term flush encompasses the terms 'break' and 'wave' and can be read as either of those terms.

Fungus: A microorganism classified as a member of the Kingdom Fungi.

Genealogical relationship: A familial relationship of descent from one or more progenitors, for example that between parents and offspring.

Genetic identity: The genetic information that distinguishes an individual, including representations of said genetic information such as, and including: genotype, genotypic fingerprint, genome sequence, genetic marker profile; "genetically identical"=100% genetic identity, "X % generically identical"=having X % genetic identity, etc.

Genotypic fingerprint: A description of the genotype at a defined set of marker loci; the known genotype.

Gill: Lamella; part of the mushroom, the hymenophore- and basidium-bearing structure.

Haploid: Having only a single complement of nuclear chromosomes; see homokaryon.

Heteroallelic: Having two different alleles at a locus; analogous to heterozygous.

Heteroallelism: Differences between homologous chromosomes in a heterokaryotic genotype; analogous to heterozygosity.

Heterokaryon: As a term of art this refers to a sexual heterokaryon: a culture which has two complementary (i.e., necessarily heteroallelic at the MAT locus) types of haploid nuclei in a common cytoplasm, and is thus functionally and physiologically analogous to a diploid individual (but cytogenetically represented as N+N rather than 2N), and which is reproductively competent (in the absence of any rare interfering genetic defects at loci other than MAT), and which exhibits vegetative incompatibility reactions with other heterokaryons; also called a strain or stock in the strain development context.

Heterokaryon compatibility: The absence of antagonism observed during physical proximity or contact between two heterokaryons that are not genetically identical; see Heterokaryon Incompatibility.

Heterokaryon incompatibility: The phenomenon of antagonism observed during physical proximity or contact between two heterokaryons that are not genetically identical; a multilocus self/non-self recognition system; i.e., a genetic system that allows one heterokaryon culture to discriminate and recognize another culture as being either self or not-self, that operates in basidiomycete heterokaryons to limit anastomosis (hyphal fusion) and cytoplasmic contact; vegetative incompatibility.

Heterokaryotic: Having the character of a heterokaryon.

Heteromixis: Life cycle involving mating between two different non-sibling haploid individuals or gametes; outbreeding.

Homoallelic: Having not more than one allele at a locus. The equivalent term in a diploid organism is 'homozygous'. Haploid lines are by definition entirely homoallelic at all non-duplicated loci.

Homokaryon: A haploid culture with a single type (or somatic lineage) of haploid nucleus (cytogenetically represented as N), and which is ordinarily reproductively incompetent, and which does not exhibit typical self/non-self incompatibility reactions with heterokaryons, and which may function as a gamete in sexually complementary anastomoses; a 'line' which, as with an inbred plant line, transmits a uniform genotype to offspring; a predominantly homoallelic line that mates well and fruits poorly is a putative homokaryon for strain development purposes; see discussion below.

Homokaryotic: Having the character of a homokaryon; haploid.

Hybrid: Of biparental origin, usually applied to heterokaryotic strains and cultures produced in controlled matings.

Hybridizing: Physical association, for example on a petri dish containing a sterile agar-based nutrient medium, of two cultures, usually homokaryons, in an attempt to achieve anastomosis, plasmogamy, and formation of a sexual heterokaryon (=mating); succeeding in the foregoing.

Hyphae: Threadlike elements of mycelium, composed of cell-like compartments.

Inbreeding: Matings that include sibling-line matings, back-matings to parent lines or strains, and intramixis; reproduction involving parents that are genetically related.

Induced mutagenesis: a non-spontaneous process of altering the DNA sequence of at least one gene locus.

Initial culture: A culture which is used as starting material in a strain development process; more particularly a strain from which an Essentially Derived Variety is obtained.

Incompatibility: See heterokaryon incompatibility.

Inoculum: A culture in a form that permits transmission and propagation of the culture, for example onto new media; specialized commercial types of inoculum include spawn and CI.

Intramixis: A uniparental sexual life cycle involving formation of a complementary 'mated' pair of postmeiotic nuclei within the basidium or individual spore.

Introgressive trait conversion: mating offspring of a hybrid to a parent line or strain such that a desired trait from one strain is introduced into a predominating genetic background of the other parent line or strain.

Lamella: see 'gill'.

Line: A culture used in matings to produce a hybrid strain; ordinarily a homokaryon which is thus homoallelic, otherwise a non-heterokaryotic (non-NSNPP) culture which is highly homoallelic; practically, a functionally homokaryotic and entirely or predominantly homoallelic culture; analogous in plant breeding to an inbred line which is predominantly or entirely homozygous.

Lineage group: see 'derived lineage group'. The set of EDVs derived from a single initial strain or variety.

Locus: A defined contiguous part of the genome, homologous although often varying among different genotypes; plural: loci. Marker assisted selection: Using linked genetic markers including molecular markers to track trait-determining loci of interest among offspring and through pedigrees.

MAT: The mating-type locus, which determines sexual compatibility and the heterokaryotic state.

Mating: The sexual union of two cultures via anastomosis and plasmogamy; methods of obtaining matings between mushroom cultures are well known in the art.

Mycelium: The vegetative body or thallus of the mushroom organism, comprised of threadlike hyphae.

Mushroom: The reproductive structure of an agaric fungus; an agaric; a cultivated food product of the same name.

Neohaplont: A haploid culture or line obtained by physically deheterokaryotizing (reducing to haploid components) a heterokaryon; a somatically obtained homokaryon.

Offspring: Descendents, for example of a parent heterokaryon, within a single generation; most often used to describe cultures obtained from spores from a mushroom of a strain.

Outbreeding: Mating among unrelated or distantly related individuals.

Parent: An immediate progenitor of an individual; a parent strain is a heterokaryon; a parent line is a homokaryon; a heterokaryon may be the parent of an F1 heterokaryon via an intermediate parent line.

Pedigree-assisted breeding: The use of genealogical information to identify desirable combinations of lines in controlled mating programs.

Phenotype: Observable characteristics of a strain or line as expressed and manifested in an environment.

Plasmogamy: Establishment, via anastomosis, of cytoplasmic continuity leading to the formation of a sexual heterokaryon.

Progenitor: Ancestor, including parent (the direct progenitor).

Selfing: Mating among sibling lines; also intramixis.

Sexual compatibility: A condition among different lines of allelic non-identity at the Mat locus, such that two lines are able to mate to produce a stable and reproductively competent heterokaryon. The opposite condition, sexual incompatibility, occurs when two lines each have the same allele at the Mat locus.

Somatic: Of the vegetative mycelium.

Spawn: A mushroom culture, typically a pure culture of a heterokaryon, typically on a sterile substrate which is friable and dispersible particulate matter, in some instances cereal grain; commercial inoculum for compost; reference to spawn includes reference to the culture on a substrate.

Spore: Part of the mushroom, the reproductive propagule.

Stem: Stipe; part of the mushroom, the cap-supporting structure.

Sterile Growth Media: Nutrient media, sterilized by autoclaving or other methods, that support the growth of the organism; examples include agar-based solid nutrient media such as Potato Dextrose Agar (PDA), nutrient broth, and many other materials.

Stipe: see 'stem'.

Strain: A heterokaryon with defined characteristics or a specific identity or ancestry; equivalent to a variety.

Targeted mutagenesis: a process of altering the DNA sequence of at least one specific gene locus.

Tissue culture: A de-differentiated vegetative mycelium obtained from a differentiated tissue of the mushroom.

Trait conversion: A method for the selective introduction of the genetic determinants of one (i.e., a single-locus conversion) or more desirable traits into the genetic background of an initial strain while retaining most of the genetic background of the initial strain. See 'Introgressive trait conversion' and 'Transformation'.

Transformation: A process by which the genetic material carried by an individual cell is altered by the incorporation of foreign (exogenous) DNA into its genome; a method of obtaining a trait conversion including a single-locus conversion.

Vegetative compatibility: The absence of the phenomenon of antagonism observed during physical proximity or contact between two heterokaryons that are not genetically identical, determined by a multilocus self/non-self recognition system that operates in basidiomycete heterokaryons to limit anastomosis (hyphal fusion) and cytoplasmic contact; Heterokaryon compatibility; the opposite of Vegetative incompatibility.

Vegetative incompatibility: The phenomenon of antagonism observed during physical proximity or contact between two heterokaryons that are not genetically identical, determined by a multilocus self/non-self recognition system that operates in basidiomycete heterokaryons to limit anastomosis (hyphal fusion) and cytoplasmic contact; heterokaryon incompatibility.

Virus-breaking: Using multiple incompatible strains, i.e. strains exhibiting heterokaryon incompatibility, successively in a program of planned strain rotation within a mushroom production facility to reduce the transmission of virus from on-site virus reservoirs into newly planted crops.

Yield: The net fresh weight of the harvest crop, normally expressed in pounds per square foot.

Yield pattern: The distribution of yield within each flush and among all flushes; influences size, quality, picking costs, and relative disease pressure on the crop and product.

With respect to the definition of homokaryon above, it is noted that homokaryons and homoallelic lines are subject to technical and practical considerations: A homokaryon in classical terms is a haploid culture which is axiomatically entirely homoallelic. In practical terms, for fungal strain development purposes, the definition is broadened somewhat to accommodate both technical limitations and cytological variation, by treating all predominately homoallelic lines as homokaryons. Technical limitations include the fact that genomes contain duplicated DNA regions including repeated elements such as transposons, and may also include large duplications of chromosomal segments due to historical translocation events. Two different *A. bisporus* genomes sequenced by the Joint Genome Institute, a U.S. federal facility, differ in estimated length by 4.4%, and in gene numbers by 8.2%, suggesting a considerable amount of DNA duplication or rearrangement within different strains of the species. No presently available genome of *A. bisporus* can completely account for the physical arrangement of such elements and translocations, and so the assembled genome sequences of haploid lines may have regions that appear to be heteroallelic using currently available genotyping methods. Cytologically, a homokaryotic offspring will ordinarily be a spore that receives one haploid, postmeiotic nucleus. However, a spore receiving two third-division nuclei from the basidium will be genetically equivalent to a homokaryon. A spore receiving two second-division 'sister' postmeiotic nuclei will be a functional homokaryon even though some distal 'islands' of heteroallelism may be present due to crossovers during meiosis. Also, a meiosis that has an asymmetrical separation of homologues can produce an aneuploid, functionally homokaryotic spore in which an extra chromosome, producing a region of heteroallelism, is present. All of these cultures are highly homoallelic and all function as homokaryons. Technological limitations make it impractical to distinguish among such cultures, and also to rule out DNA segment duplication as an explanation for limited, isolated regions of the genome sequence assembly that appear to be heteroallelic. Therefore, in the present application, the use of the term 'homoallelic' to characterize a line includes entirely or predominately homoallelic lines, and cultures described in this way are functional homokaryons, are putatively homokaryotic, and are all defined as homokaryons in the present application.

*Agaricus bisporus* mushroom line J14756-s3 is a haploid, homokaryotic filamentous basidiomycete culture which in vegetative growth produces a branching network of hyphae, i.e., a mycelium. Growth can produce an essentially two-dimensional colony on the surface of solidified (e.g., agar-based) media, or a three-dimensional mass in liquid or solid-matrix material.

The morphological and physiological characteristics of line J14756-s3 in culture on Difco brand PDA medium, which is a standard culture medium, are provided as follows. Line J14756-s3 growing on PDA medium in an 8.5 cm diameter Petri dish produced a white or light brown-yellow colored irregularly lobate colony with a roughly circular overall outline that increased in diameter by (1.00-1.26-) 1.27 (-1.28-1.46) mm/day during dynamic equilibrium-state growth between days 8 and 40 after inoculation using a 5.5-6 mm diameter circular plug of the culture on PDA as inoculum. Hyphae of the culture on Difco PDA were irregular and about cylindrical, measured 115-215×2.3-3.1 um, and exhibited a wide range of branching angles from about 10 to 90 degrees off the main hyphal axis. The line has shown uniformity and stability in culture. The line has been increased by transfer of pure inocula into larger volumes of sterile culture media. No variant traits have been observed or are expected in line J14756-s3.

Several useful stocks have contributed to the genome of line J14756-s3. The homokaryotic line J14756-s3 is a selection obtained from a $6^{th}$ generation Sylvan experimental hybrid strain incorporating four different wild germ plasm stocks and three different commercial strains via a total of eight separate matings. Each progenitor of J14756-s3 has contributed distinctive genetic markers to the pedigree. The markers incorporated in the genotype of haploid line J14756-s3 are similarly transmitted into F1 hybrid descendents of J14756-s3, and constitute one of the two nuclear genomes present in each of those F1 heterokaryotic strains.

Genetic identity (e.g., genotype), genealogy, and pedigree are all inextricably interrelated in a strain development or breeding program, as in the cultures of the present invention. The following information on life cycles and heterokaryotic and homokaryotic genotypes, and on parents, offspring, hybrids and descended strains, and derived strains (i.e., EDVs), may help to clarify relationships and expectations.

Mushroom-forming fungi exhibit an alternation of generations, from heterokaryotic (N+N, with two haploid nuclei, functionally like the 2N diploid state) to homokaryotic (1N) and further upon mating to become heterokaryotic again. In most eukaryotes, a parent is conventionally considered to be either diploid or heterokaryotic. The haploid 'generation' is often, but not always, termed a gamete (e.g., pollen, sperm). In fungi, which are microorganisms, the haploid generation can live and grow indefinitely and independently, for example in laboratory cell culture; while these haploid homokaryons function as gametes in matings, they are equivalent to inbred lines (e.g., of plants) and are more easily referred to as parental lines (of hybrid descendants). Herein, the term 'parental' refers to the culture that is a, or the, direct progenitor of another culture within the alternating generations of the sexual lifecycle. The term 'line' refers more narrowly to a haploid (N) homoallelic culture within the lifecycle. The N+N heterokaryon resulting from a mating, or comprising a breeding stock, or comprising a culture used to produce a crop of mushrooms, may be called a 'strain'.

If one parental line carries allele 'p' at a particular locus, and the other parental line carries allele 'q', the F1 hybrid resulting from a mating of these two lines will carry both alleles, and the genotype can be represented as 'p/q' (or 'pq', or 'p+q'). Sequence-characterized markers are codominant and both alleles will be evident when an appropriate sequencing protocol is carried out on cellular DNA of the hybrid. The profile of line J14756-s3 can therefore be used to identify hybrids comprising line J14756-s3 as a parent line, since such hybrids will comprise two sets of alleles, one of which sets will be from, and match that of, line J14756-s3. The match can be demonstrated by subtraction of the second allele from the genotype, leaving the J14756-s3 allele evident at every locus. A refinement of this approach is possible with hybrids of Agaricus bisporus as a consequence of the heterokaryon (N+N) condition existing in hybrids. The two haploid nuclei can be physically isolated by various known techniques (e.g., protoplasting) into 'neohaplont' subcultures, and each may then be characterized independently. One of the two neohaplont nuclear genotypes from the F1 hybrid will be that of line J14756-s3, demonstrating its use in the mating step of the method, and its presence in the hybrid.

A heterokaryotic selfed offspring of an F1 hybrid that itself has a 'p/q' genotype will in the example have a genotype of 'p/p', 'q/q', or 'p/q'. Two types of selfing lead to differing expectations about representation of alleles of line J14756-s3 present in the F1 hybrid in the next heterokaryotic generation. When two randomly obtained haploid offspring from the same F1 hybrid, derived from individual spores of different meiotic tetrads, are mated (i.e., in intertetrad selfing), representation of the line J14756-s3 marker profile in each recombined haploid parental line and in each sib-mated heterokaryon will be 50% on average, and slightly more than 75% (to about 85%) of heteroallelism present in the F1 hybrid will on average be retained in the sib-mated heterokaryon (the expectation over 75% is due to the mating requirement for heteroallelism at the mating type locus (MAT) on Chromosome 1). Distinctively, in addition, Agaricus bisporus regularly undergoes a second, characteristic, spontaneous intra-tetrad form of selfing called intramixis, producing heterokaryotic postmeiotic spores carrying two different recombined haploid nuclei having complementary, heteroallelic MAT alleles. An offspring developing from any one of these spores is a postmeiotic self-mated heterokaryon with ca. 100% retention of the heteroallelism present in the single F1 parent around all 13 pairs of centromeres. In theory this value would decrease to an average of 66.7% retention of F1 heteroallelism for distal markers unlinked to their centromeres; however empirical observations suggest higher rates of retention even for such distal markers, in conjunction with limited crossing-over. Transmission of the line J14756-s3 marker profile in such selfed offspring may be incomplete by a small percentage (typically 0-10%) due to the effects of infrequent meiotic crossovers, while representing 50% on average of the resulting heterokaryotic genome. Both types of selfed offspring are considered to be Essentially Derived Varieties (EDVs) of the initial F1 hybrid, and the latter type comprises most (often 95-100%) of the genotype of the F1, and may express a very similar phenotype to that of the F1 hybrid.

There is general concordance among accepted definitions of an EDV, although some particulars may vary; one example of a definition applicable to plant varieties is provided by the US Plant Variety Protection Act (revised edition, February 2006). The definition employed herein, i.e., "a culture derived from an initial culture such that the resulting culture has present at least 75% of the genome or genotype of the initial culture", is congruent with the term as it is widely understood. Several 'essential derivation' methods of obtaining cultures that are EDVs of a single initial culture of A. bisporus are given above. Repeated mating back to the initial culture to introgress a single trait into the genetic background of an initial variety or strain is called introgressive trait conversion, and produces an EDV of the initial strain. DNA-mediated transformation of A. bisporus has been reported in the prior art. Transformation may introduce a single new gene or allele into the genome of an initial variety.

Now, with respect to the invention and as noted hereinabove, the present invention relates to at least a homokaryotic line, and more specifically, a culture comprising at least one set of chromosomes of an Agaricus bisporus line designated J14756-s3, and methods for using the line designated J14756-s3. A culture of the line designated J14756-s3 has been deposited with the Agricultural Research Services Culture Collection (NRRL) 1815 North University Street, Peoria, Ill. 61604 USA ("NRRL") as Accession No. 67317. The J14756-s3 line is a homokaryon and its genome and genotype are haploid and thus is entirely homoallelic (although some limited regions of duplicated DNA may be present in its genome).

A culture comprising at least one set of chromosomes of an Agaricus bisporus line designated J14756-s3 may be either a homokaryon or a heterokaryon selected from the group consisting of: (a) line J14756-s3, (b) a culture having all morpholological and physiological characteristics of line J14756-s3, (c) a culture having full genotypic identity in agreement with the allelic genotype of J14756-s3 presented in Tables I and II, (d) a culture having at least 75% genotypic identity with J14756-s3, and (e) an F1 hybrid having J14756-s3 as a direct parent. Essentially Derived Varieties of an initial culture of the invention will have between 100% and 75% genotypic identity with said initial culture, which is selected from the group of initial cultures comprising: line J14756-s3, a line having all morpholological and physiological characteristics of line J14756-s3, a line having genotypic identity in agreement with the allelic genotype of J14756-s3 presented in Tables I and II, a line having at least a 75% genetic identity with line J14756-s3, an F1 hybrid having a homokaryotic line culture comprising at least one set of chromosomes of an Agaricus bisporus line designated J14756-s3 as a direct parent, and an EDV of any culture of the invention.

Mushroom cultures are most reliably identified by their genotypes, in part because successful cultivar strains are required by the market to conform to a narrow phenotypic range. The genotype can be characterized through a genetic marker profile, which can identify isolates (clones or subcultures) of the same line, strain or variety, or a related variety including a variety derived entirely from an initial variety (i.e., an Essentially Derived Variety), or can be used to determine or validate a strain development pedigree over generations.

Means of obtaining genetic marker profiles using diverse techniques including whole genome sequencing are well known in the art. The whole genomic sequence of line J14756-s3 has been obtained by Sylvan America, Inc., and consequently, about 95% (about 30.2 Mb) of the entire DNA sequence genotype of line J14756-s3 is known to the Assignee with certainty. The total number of markers distinguishing line J14756-s3 that are known to the assignee is about 279,000. A brief excerpt of the genotype of line J14756-s3 at numerous sequence-characterized marker loci distributed at intervals along each of the 13 chromosomes is provided in Table I.

TABLE I

| Scaffold | Position of SNP [H97 V2.0 ref. coordinates] | Cultures: H97 | Wild Line | J14756-s3 | J15051 |
|---|---|---|---|---|---|
| 1 | 99995 | CTACATTGA | CTAC*G*TTGA | CTAC*G*TTGA | CTAC*G*TTGA |
| 1 | 349966 | AAGGTGGTT | AAGG*C*GGTT | AAGG*C*GGTT | AAGG*C*GGTT |
| 1 | 600059 | TTTTTTTT- | TTTTTTTT*C* | TTTT*C*TTTT- | TTTT*y*TTT*C* |
| 1 | 850014 | CCTTTTCAC | *T*CTT*G*TCAC | *T*CTT*G*TCAC | *T*CTT*G*TCAC |
| 1 | 1099971 | GTCGACACC | GTCGACACC | GTCG*G*CACC | GTCG*r*CACC |
| 1 | 1350278 | GGAGAGTCG | GGAGAGTCG | GGAG*GT*TCG | GGAG*rk*TCG |
| 1 | 1599956 | AATAAGCGC | AATAAGCGC | AATA*G*GCGC | AATA*r*GCGC |
| 1 | 1850032 | CGAGTAATT | CGAGAATT | CGAG*C*AATT | CGAG*C*AATT |
| 1 | 2119049 | ACAATCCAA | ACAA*CT*CAA | ACAA*CT*CAA | ACAA*CT*CAA |
| 1 | 2400243 | ACTTCATGA | ACTT*G*ATGA | ACTT*G*ATGA | ACTT*G*ATGA |
| 1 | 2612870 | AATAGGAGT | AATAGGAGT | AATA*A*GAGT | AATA*r*GAGT |
| 1 | 2858975 | GCCGTTCTT | GCCG*C*TCTT | GCCG*C*TCTT | GCCG*C*TCTT |
| 1 | 2804522 | GAAGACGAC | GAAG*GC*GAC | GAAG*GC*GAC | GAAG*GC*GAC |
| 1 | 3047987 | AAGGGGGGG | AAGG*A*GGGG | AAGGGGGGG | AAGG*r*GGGG |
| 1 | 3212182 | CACTACGTG | CACTGCGTG | CACTACGTG | CACT*r*CGTG |
| 1 | 3256057 | TATCTGTTT | TATC*C*GTTT | TATC*C*GTTT | TATC*C*GTTT |
| 2 | 101820 | ATTAAAGAT | ATTAAAGAT | ATTAAAGAT | ATTAAAGAT |
| 2 | 350156 | TCGGGGTG | TCGG*A*GGTG | TCGGGGTG | TCGG*r*GGTG |
| 2 | 600112 | ATGTATACG | ATGT*G*TACG | ATGTATACG | ATGT*r*TACG |
| 2 | 850338 | TGGTGCTAA | TGGT*T*CTAA | TGGTGCTAA | TGGT*k*CTAA |
| 2 | 1099413 | CCTGACTCA | CCTG*G*CTCA | CCTGACTCA | CCTG*r*CTCA |
| 2 | 1349512 | CTCAGCAGT | CTCA*A*CAGT | CTCAGCAGT | CTCA*r*CAGT |
| 2 | 1600085 | CACAATGCC | CACA*TT*GCC | CACAATGCC | CACA*w*TGCC |
| 2 | 1901773 | ACTCGAATT | ACT*AA*AATT | ACTC*A*AATT | ACT*m*AATT |
| 2 | 2150201 | GTCGTAGGT | GTCG*A*AGGT | GTCGTAGGT | GTCG*w*AGGT |
| 2 | 2400281 | TCAAAACCC | TCAA*C*ACCC | TCAA*C*ACCC | TCAA*C*ACCC |
| 2 | 2650136 | ATAATTCCT | ATAA*G*TCCT | ATAATTCCT | ATAA*k*TCCT |
| 2 | 2903620 | ACTAAAAGA | ACTAAAAGA | ACTAAAAGA | ACTAAAAGA |
| 2 | 3048019 | GTCCGCTGC | GTCCGCTGC | GTCCGCTGC | GTCCGCTGC |
| 3 | 57117 | TATAGCAGT | TAT*GA*CAGT | TAT*GA*CAGT | TAT*GA*CAGT |
| 3 | 65650 | GGCGCTTTT | GGCG*G*TTTT | GGCG*G*TTTT | GGCG*G*TTTT |
| 3 | 119181 | TTTATACTC | TTTATACTC | TTTATACTC | TTTATACTC |
| 3 | 250112 | GCAGGAGAG | GCC*GA*AGAG | GCAGGAGAG | G*Cm*GAGAG |
| 3 | 750000 | GTCCGGCCA | GTCCGGCCA | GTCGGCCA | GTCCGGCCA |
| 3 | 750074 | AGTTTTTTC | AGTT*A*TTTC | AGTTTTTTC | AGTT*w*TTTC |
| 3 | 1250000 | TTTTTCCGG | TTTTTCCGG | TTTTTCCGG | TTTTTCCGG |
| 3 | 1250161 | AGTCTCCTT | AGTC*C*CCTT | AGTCTCCTT | AGTC*y*CCTT |
| 3 | 1750000 | ACGCCTGAC | ACGCCTGAC | ACGCCTGAC | ACGCCTGAC |
| 3 | 1750033 | TTTTTTGCT | TTTT*G*TGCT | TTTTTTGCT | TTTT*k*TGCT |
| 3 | 2250000 | CGTGGCGAT | CGTGGCGAT | CGTGGCGAT | CGTGGCGAT |
| 3 | 2250027 | TGTATCAAG | TGT*GC*CAAG | TGTATCAAG | TGT*ry*CAAG |
| 3 | 2520748 | TAATTCCAC | TAAT*G*CCAC | TAATTCCAC | TAAT*k*CCAC |
| 4 | 100004 | GAGTGATAA | GAGTGATAA | GAGTGATAA | GAGTGATAA |
| 4 | 490648 | CGATCGCGT | CGAT*T*GCGT | CGATCGCGT | CGAT*y*GCGT |
| 4 | 598147 | GATCGACAG | GATCAACAG | GATCGACAG | GATC*r*ACAG |
| 4 | 852119 | CGAATATTC | CGAATATTC | CGAATATTC | CGAATATTC |
| 4 | 1100085 | GATGCCGAA | GATG*A*CGAA | GATGCCGAA | GATG*m*CGAA |
| 4 | 1350536 | CGAACTCGG | CGAA*AT*CGG | CGAACTCGG | CGAA*mT*CGG |
| 4 | 1599885 | GATACTTGC | GATACTTGC | GATACTTGC | GATACTTGC |
| 4 | 1850288 | ATTCGTGTA | ATTC*A*TGTA | ATTCGTGTA | ATTC*r*TGTA |
| 4 | 2100356 | TCAGAGACC | TCAGAGACC | TCAG*G*GACC | TCAG*r*GACC |
| 4 | 2284257 | TCTGGACTG | TCTG*A*ACTG | TCTG*A*ACTG | TCTG*r*ACTG |
| 5 | 100211 | TCCTTGAAT | TCCT*G*GAAT | TCCT*G*GAAT | TCCT*G*GAAT |
| 5 | 350872 | GGCGTGCCC | GGCGTGCCC | GGCG*C*GCCC | GGCG*y*GCCC |
| 5 | 599922 | CGTCATTCA | CGTCATTCA | CGTC*G*TTCA | CGTC*r*TTCA |
| 5 | 851262 | TAATTCTCT | TAAT*CG*TCT | TAAT*CG*TCT | TAAT*CG*TCT |
| 5 | 1099776 | ACATTGACA | ACAT*C*GACA | ACATTGACA | ACAT*y*GACA |
| 5 | 1352539 | TTGTGATCC | TTGTGATCC | TTGT*TG*TCC | TTGT*kr*TCC |
| 5 | 1599904 | AACTTCCTT | AACT*C*CCTT | AACT*C*CCTT | AACT*C*CCTT |
| 5 | 1851458 | AAATAATCC | AAAT*TC*TCC | AAAT*TC*TCC | AAAT*TC*TCC |
| 5 | 2100025 | CCCTTAGTC | CCCTTAGTC | CCCT*C*AGTC | CCCT*y*AGTC |
| 5 | 2278878 | GGTCAAAAA | GGTCAAAAA | *A*GTCAAAAA | *r*GTCAAAAA |
| 6 | 106294 | GCCATCTCG | GCCA*C*CTCG | GCCATCTCG | GCCA*y*CTCG |
| 6 | 350337 | CATTTGGTT | CATT*C*GGTT | CATTTGGTT | CATT*y*GGTT |
| 6 | 600047 | GGAGCATTT | GGAG*T*ATTT | GGAGCATTT | GGAG*y*ATTT |
| 6 | 849985 | AGTTCAGGA | AGTTCAGGA | AGTTCAGGA | AGTTCAGGA |

TABLE I-continued

| Scaffold [H97 V2.0 ref. coordinates] | Position of SNP | Cultures: H97 | Wild Line | J14756-s3 | J15051 |
|---|---|---|---|---|---|
| 6 | 1098535 | CAAAGATTG | CAAA*A*ATTG | CAAAGATTG | CAAA*r*ATTG |
| 6 | 1349453 | TGTCGGTAG | TGTC*AA*TAG | TGTCGGTAG | TGTC*rr*TAG |
| 6 | 1600000 | AAACCTGGA | AAACCTGGA | AAACCTGGA | AAACCTGGA |
| 6 | 1764645 | AACCAGATT | AACC*G*GATT | AACCGGATT | AACC*r*GATT |
| 6 | 2000087 | GATTTTGCG | GATTTTGCG | GATTTTGCG | GATTTTGCG |
| 6 | 2252662 | GGGTTGGTA | GGGT*C*GGTA | GGGTTGGTA | GGGT*y*GGTA |
| 7 | 100284 | GAAATTCAG | GAAA*C*TCAG | GAAATTCAG | GAAA*y*TCAG |
| 7 | 350044 | ATATTCTTT | ATAT*C*CTTT | ATATTCTTT | ATAT*y*CTTT |
| 7 | 600111 | CAATTATTA | CAAT*C*ATTA | CAATTATTA | CAAT*y*ATTA |
| 7 | 850246 | TGACGCATA | TGACGCATA | TGACGCATA | TGACGCATA |
| 7 | 1100248 | TCACGGAAG | TCAC*A*GAAG | TCACGGAAG | TCAC*r*GAAG |
| 7 | 1350089 | CTTTTCCCC | CTTTTCCCC | CTTTTCCCC | CTTTTCCCC |
| 7 | 1605047 | ATACTTGGC | ATACTTG*AC* | ATACTTGGC | ATACTTG*rc* |
| 7 | 1860993 | GTCAACCGG | GTCA*T*CCGG | GTCAACCGG | GTCA*w*CCGG |
| 7 | 1898793 | TCCGCATAA | TCCGCATAA | TCCGCATAA | TCCGCATAA |
| 7 | 1991505 | TCTACGGTT | TCTACGGTT | TCTACGGTT | TCTACGGTT |
| 8 | 350000 | ATTGACGCG | ATTG*G*GCG | ATTG*G*CGCG | ATTG*G*CGCG |
| 8 | 610549 | GAACTTGAT | GAA*TA*CGAT | GAA*T*TTGAT | GA*Twy*GAT |
| 8 | 1100000 | CATACGATC | CATACGATC | CATACGATC | CATACGATC |
| 8 | 1100546 | GCCCCAGAA | GCCCCAGAA | GCCC*G*AGAA | GCCC*s*AGAA |
| 8 | 1350000 | AGCTTAACA | AGCTTAACA | AGCTTAACA | AGCTTAACA |
| 8 | 1350240 | ACGGGTACT | ACGG*A*TACT | ACGGGTACT | ACGG*r*TACT |
| 8 | 1600100 | CTGAACCCT | CTGAACCCT | CTGAACCCT | CTGAACCCT |
| 9 | 100105 | CTCAACCGA | CTCAACCGA | CTCA*G*CCGA | CTCA*r*CCGA |
| 9 | 352455 | AGTCCTCCA | AGTCCTCCA | AGTC*TC*CCA | AGTC*yy*CCA |
| 9 | 599950 | TGGTATCCC | TGGTATCCC | TGGT*G*TCCC | TGGT*G*TCCC |
| 9 | 1010845 | GGGTGGTGA | GGGTGGTGA | GGGT*A*GTGA | GGGT*r*GTGA |
| 9 | 1244202 | GATGAAGAT | GATGAAGAT | GATGA*G*GAT | GATG*r*AGAT |
| 9 | 1504476 | TACTGTACC | TACTGTACC | TACT*A*TACC | TACT*r*TACC |
| 9 | 1656962 | TATCTACTG | TATCTACTG | TATCTACTG | TATCTACTG |
| 10 | 100438 | AATTAATTT | *G*ATTAATTT | AATTAATTT | *r*ATTAATTT |
| 10 | 350030 | GCGGCTCAA | GCGG*T*TCAA | GCGG*T*TCAA | GCGG*T*TCAA |
| 10 | 600032 | TTACACTGG | TTACACTGG | TTACACTGG | TTACACTGG |
| 10 | 850000 | TCGGTCGGA | TCGGTCGGA | TCGGTCGGA | TCGGTCGGA |
| 10 | 860249 | CCGCAAATT | CCGC*G*AATT | CCGCAAATT | CCGC*r*AATT |
| 10 | 1173178 | ATCCCCAAT | ATCC*T*CAAT | ATCC*T*CAAT | ATCC*T*CAAT |
| 10 | 1303902 | TGATTTACT | TGATTTACT | TGATTTACT | TGATTTACT |
| 10 | 1490452 | AATCAGATG | AATCAGATG | AATCAGATG | AATCAGATG |
| 11 | 101855 | CCAGCCTGT | CCAG*T*CTGT | CCAGCCTGT | CCAG*y*CTGT |
| 11 | 350000 | GTCAGCAAG | GTCAGCAAG | GTCAGCAAG | GTCAGCAAG |
| 11 | 350025 | GATAAAACA | GATAAAACA | GATA*T*AACA | GATA*w*AACA |
| 11 | 600000 | ATGGGCGCG | ATGGG*A*GCG | ATGGG*A*GCG | ATGGG*r*GCG |
| 11 | 929659 | GGAATATCA | GGAAG*T*TCA | GGAATATCA | GGAA*kw*TCA |
| 11 | 1100608 | AGTGGTCTT | AGTGGTCTT | AGTG*A*TCTT | AGTG*r*TCTT |
| 11 | 1240230 | ACAAGTTTC | ACAA*A*TTTC | ACAAGTTTC | ACAA*r*TTTC |
| 12 | 100000 | CCTTCTAGT | CCTTCTAGT | CCTTCTAGT | CCTTCTAGT |
| 12 | 109790 | GTCTGCACC | GTCT*A*CACC | GTCTGCACC | GTCT*r*CACC |
| 12 | 1000000 | CGAGGAGGA | CGAGGAGGA | CGAG*A*AGGA | CGAG*r*AGGA |
| 13 | 100697 | ACGTCTTTA | ACGTCTTTA | ACGTCTTTA | ACGTCTTTA |
| 13 | 370521 | TTTGAGTCA | TTTG*T*GTCA | TTTG*T*GTCA | TTTG*T*GTCA |
| 13 | 604345 | CTTCAGCAT | CTTCAGCAT | CTTCAGCAT | CTTCAGCAT |
| 13 | 850249 | GGCTAGTAA | GGCTAGTAA | GGCTAGTAA | GGCTAGTAA |
| 14 | 113109 | AGGGAAATA | AGGG*G*AATA | AGGGAAATA | AGGG*r*AATA |
| 14 | 372086 | CGATCCCTT | CGAT*T*CCTT | CGATCCCTT | CGAT*y*CCTT |
| 14 | 725684 | ATGAGTTCG | ATGAGTT*T*G | ATGA*A*TTCG | ATGA*rTTy*G |
| 15 | 150013 | GTGGCCCGT | GTGG*A*CCGT | GTGGCCCGT | GTGG*m*CCGT |
| 15 | 449860 | GAATTTCGG | GAATTTCGG | GAATTTCGG | GAATTTCGG |
| 16 | 205778 | CAAGGTCTG | CAAG*A*TCTG | CAAG*A*TCTG | CAAG*A*TCTG |
| 16 | 400000 | CCTCGGATT | CCTCGGATT | CCTCGGATT | CCTCGGATT |
| 16 | 403998 | CCAAGTACG | CCAA*A*TACG | CCAAGTACG | CCAA*r*TACG |
| 17 | 120000 | TATTCTTCA | TATTCTTCA | TATTCTTCA | TATTCTTCA |
| 17 | 134676 | TTGCCCAGC | TTGC*T*CAGC | TTGCCCAGC | TTGC*y*CAGC |
| 17 | 338415 | TGAGAAGCC | TGAGAAGCC | TGAGAAGCC | TGAGAAGCC |
| 17 | 449833 | ATCAGACAA | ATCA*A*CAA | ATCA*A*ACAA | ATCA*A*ACAA |

TABLE I-continued

| Scaffold [H97 V2.0 ref. coordinates] | Position of SNP | Cultures: | | | |
|---|---|---|---|---|---|
| | | H97 | Wild Line | J14756-s3 | J15051 |
| 18 | 101884 | ATTACGGAC | ATTACGGAC | ATTACGGAC | ATTACGGAC |
| 18 | 112940 | GCGGGTGGG | GCGG*C*TGGG | GCGGGTGGG | GCGG*s*TGGG |
| 19 | 98520 | GCTATTGGG | GCTATTGGG | GCTATTGGG | GCTATTGGG |
| 19 | 98782 | AAAATTGTT | AAAA*G*TGTT | AAAATTGTT | AAAA*k*TGTT |

While many types of molecular markers are known, and can be used, all of these ultimately derive from the primary DNA sequence of the genome. The essential genotype of a line or strain is embodied in its genomic DNA sequence. The marker profile presented in Table I represents selected short segments of the genome sequence of line J14756-s3, at loci which are known to have differing sequences among other lines and strains, selected at widely spaced intervals spanning the entire nuclear genome. Commercial sequencing providers and commercial technologies such as Illumina MiSeq, among others, may be used to obtain whole-genome sequences from total cellular DNA preparations. Other techniques for obtaining genotype profiles may also be used as appropriate. All valid and appropriate techniques will, at a sufficient level of application, produce the same results.

Table I presents a genetic identity 'fingerprint' excerpted from the SNP (Single Nucleotide Polymorphism) genotype of the entire genome sequences of line J14756-s3, of standard reference line H97 (Morin et al. 2012), and of the F1 hybrid. J15051 strain descended from line J14756-53 via a mating of J14756-53 with a second, wild line, line BP-1-s53. It will be appreciated that the use of J14756-s3 to provide strain J15051 is but one example of the F1 hybrid generation, it being noted that J14756-s3 has been used in at least 28 matings with at least 28 other lines of *Agaricus bisporus*, for example lines B13597-s67, s98, s99, s51, s90, s100, B12998-s9, s14, s30, s34, s39, s40, s44, s80; J11875-s4, s7; B14528-s16a, s17, s18; BP-1-s13, s53, s99, s102, s51, s66, s90, s107, s121, to produce at least 28 unique, novel F1 hybrid strains including: J15045, J15051, J15057, J15063, J15279, J15286, J15293, J15300, J15307, J15314, J15321, J15328, J15335, J15344, J15353, J15362, J15371, J15380, J15618, J15619, J15620, J15621, J15622, J16550, J16562, J16604, J16620, and J16636. It is also possible to produce novel F1 hybrids using many other lines in matings to J14756-s3, including the following lines that are available in public culture collections: H97 (=NRRL 50894, with allele Mat-1), B12998-s39 (=NRRL 50899, with allele Mat-5); Somycel 76-s39 (=NRRL 50905, with allele Mat-3). Line 114756-s3 will mate with any second line of *Agaricus bisporus* to produce an F1 hybrid heterokaryon, except in the case where the second line shares the same Mat-2 allele, which is a general sexual incompatibility behavior that is well known in the art.

The IUPAC nucleotide and so-called "ambiguity" codes, which are actually heteroallelism codes when used to represent a heterokaryon or diploid genotype, are used in Table I to represent heteroallelic DNA sequence positions, wherein each of two alleles incorporates a different nucleotide at a particular position, in the observed 9-base DNA marker sequences reported above, each of which represents a genotypic marker locus. The identity of each marker locus is specified by the scaffold and SNP position information derived from the H97 V2.0 standard reference genome sequence published by the U.S. Department of Energy Joint Genome Institute (Morin et al. 2012). Distinctions between the homoallelic genotypes of line J14756-s3 and line H97 are evident, as is the composite nature of the example heteroallelic genotype of F1 hybrid strain J15051, in which the presence of the genome of J14756-s3 is evident, as expected, by virtue of perfect conformity, with no conflicts, with the presence of the alleles known to be present in strain J15051. A brief description of the genotype of line J14756-s3 and strain B15051 at a further six unlinked marker loci is provided below. The six markers identified below have been used to provide genotypic fingerprint data on line J14756-s3, strain J15051, and other lines and strains. They are the six most commonly referenced marker loci in the industry and are considered art standard designations in that all six of the marker loci have been used, in one form or another, to characterize the genotype of *Agaricus* strains in at least one public source publication. Because the B15051 heterokaryon incorporates two sets of chromosomes, one from each haploid parent, there are two allelic copies (two characters or elements of the genotype) at each marker locus. The brief genotype excerpt provided below therefore consists of 6 or 12 alleles, characters or elements for the line or strain respectively. The brief genotype excerpt was prepared by Sylvan America, Inc. using targeted Polymerase Chain Reactions to amplify genomic regions bracketing the defined markers from each of the culture DNAs. The PCR primers identified for each defined marker regions below are provided to establish how the Applicant obtained the information. It will be appreciated however that any suitable PCR primers that bracket the defined marker regions may be used for this purpose. methods of designing and using suitable PCR primers are well known in the art. The amplified PCR product DNA was sequenced by a contractor, Eurofins, using methods of their choice, and the genotypes were determined by direct inspection of these sequences in comparison to Applicant's database of reference marker/allele sequences.

Description of p1n150/Mat Marker

The 5' end of this marker segment begins at position 1 with the first "T" in the sequence TCCCAAGT, corresponding to H97 JGI V2.0 Scaffold 1 position 868615 (Morin et al. 2012) and extending in a reverse orientation (relative to the scaffold orientation) for ca. 600 nt in most alleles; an insertion of the Abr1 transposon at position 207 in the DNA of allele 1T has produced a longer segment. At present, 9 alleles incorporating at least 30 polymorphic positions have been documented from diverse strains in Sylvan America's breeding collection.

The "p1n150-3G-2" marker is a refinement of the p1n150 marker reported on Chromosome 1 by Kerrigan, R. W., et al. "Meiotic behavior and linkage relationships in the secondarily homothallic fungus *Agaricus bisporus*." *Genetics* 133, 225-236 (1993), and shown to be linked to the MAT (mating type) locus by Xu et al., "Localization of the mating type gene in *Agaricus bisporus*." *App. Env. Microbiol.* 59(9): 3044-3049 (1993) and has also been used in other published studies. While several different primers can be and have been used to amplify segments of DNA in which the p1n150-3G-2 marker is present and from which it can be sequenced, digested, electrophoretically characterized, or otherwise analyzed, the primer sequences employed by the inventors for the development of the disclosed data are: Forward: 5'-aggcrycccatcttcasc-3' (SEQ ID NO. 1); Reverse: 5'-gttcgacgacggactgc-3' (SEQ ID NO. 2), with 35 PCR cycles, 56 C anneal temperature, 1 min. extension time.

Alleles present in the J14756-s3/J15051 immediate pedigree, or in commercially cultivated brown strains, include alleles 1T, 2, 3, and 5, characterized as follows (using the format: nucleotide base character @ alignment position, based on alignment of alleles 2, 3, and 5, and the alignable portions of allele 1T):

Allele 1T: insertion of Abr1 transposon of 320 nt @ 206^207; 'A' @ 321; 'T' @ 327; 'C' @ 374; 'G' @ 378; 'G' @ 422; 'C' @ 431; 'G' @ 472; etc.

Allele 2: no Abr1 insertion; 'A' @ 321; 'C' @ 327, 'C' @ 374; 'C' @ 378; 'G' @ 422; 'T' @ 431; 'G' @ 472; etc.

Allele 3: no Abr1 insertion; 'A' @ 321; 'T' @ 327, 'G' @ 374; 'C' @ 378; 'G' @ 422; 'T' @ 431; 'A' @ 472; etc.

Allele 5: no Abr1 insertion; 'G' @ 321; 'C' @ 327, 'C' @ 374; 'C' @ 378; 'G' @ 422; 'T' @ 431; 'G' @ 472; etc.

Because of linkage to the MAT locus, which is obligately heteroallelic in fertile heterokaryons, genotypes of all known and expected heterokaryons at p1n150-G3-2 are also heteroallelic.

The J14756-s3 homokaryon line carries allele 2. The wild homokaryon line carries allele 5. The J15051 heterokaryon strain has an '2/5' heteroallelic genotype for the p1n150-G3-2 marker locus (and also for the linked Mat locus), indicating the presence of alleles 2 and 5, which distinguishes it from the OFB strains, which have a '1T/3' genotype, and also from the 28C strain (and therefore from Heirloom, 28Cc, etc.), which has a '1T/5' genotype, and lacks allele 2, as well as from other strains which are homoallelic and/or which carry other different alleles.

Description of the ITS (=ITS 1+2 Region) Marker

The ITS segment is part of the nuclear rDNA region, which is a cassette that is tandemly repeated up to an estimated 100 times in the haploid genome of *A. bisporus*. Therefore there is no single precise placement of this sequence in the assembled H97 genome, and in fact it is difficult or impossible to precisely assemble the sequence over all of the tandem repeats. Three cassette copies were included on scaffold 10 of the H97 JGI V2.0 assembly, beginning at position 1612110; a partial copy is also assembled into scaffold 29 (Morin et al. 2012). The 5' end of this marker segment begins at position 1 with the first "G" in the sequence GGAAGGAT, and extending in a forward orientation (relative to the scaffold orientation) for ca. 703-704 nt in most alleles. At present, more than 9 alleles incorporating at least 11 polymorphic positions have been documented from diverse strains in Assignee's breeding collection.

The ITS marker has been adopted as the official 'barcode' sequence for all fungi (Schoch et al., Fungal Barcoding Consortium, "Nuclear ribosomal internal transcribed spacer (ITS) region as a universal DNA barcode marker for Fungi." Proc. Nat. Acad. Sci. pnas.org/cgi/content/short/1117018109 (2012), and has been used in innumerable publications, including Morin et al., "Genome sequence of the button mushroom *Agaricus bisporus* reveals mechanisms governing adaptation to a humic-rich ecological niche." *Proc. Nat'l Acad. Sci.* USA 109:1.7501-17506 (2012) on the complete *A. bisporus* genome sequence. White et al. (1990), Amplification and direct sequencing of fungal ribosomal RNA genes for phylogenetics. In: PCR Protocols: a guide to methods and applications. (Innis M A, Gelfand D H, Sninsky J J, White T J, eds). Academic Press, New York, USA: 315-322, published many primer sequences for the ITS marker, of which the inventors use primers ITS1: 5'-tccgtaggtgaaccggcgg-3' (SEQ. ID NO. 3) and ITS4: 5'-tcctccgcttattgatatgc-3' (SEQ. ID NO. 4), with 35 PCR cycles, 56C anneal temperature, 1 min. extension time.

Alleles present in the J14756-s3/J15051 immediate pedigree, or in commercially cultivated brown strains, include alleles I1, I2, I3, and I4 characterized as follows (using the format: nucleotide base character @ alignment position, based on alignment of 9 alleles):

Allele I1: 'A' @ 32; 'C' @ 52; 'C' @ 150; 'T' @ 153; 'T' @ 461; 'T' @ 522; 'T' @ 563; etc.

Allele I2: 'A' @ 32; 'T' @ 52; 'C' @ 150; 'T' @ 153; 'T' @ 461; 'T' @ 522; 'T' @ 563; etc.

Allele I3: 'A' @ 32; 'C' @ 52; 'C' @ 150; 'T' @ 153; 'T' @ 461; 'C' @ 522; 'C' @ 563; etc.

Allele I4: 'A' @ 32; 'C' @ 52; 'C' @ 150; 'T' @ 153; 'A' @ 461; 'C' @ 522; 'C' @ 563; etc.

Allele I5: 'G' @ 32; 'C' @ 52; 'T' @ 150; 'C' @ 153; 'A' @ 461; 'C' @ 522; 'C' @ 563; etc.

The J14756-s3 homokaryon line carries allele I5. The wild homokaryon line carries allele I1. The J15051 heterokaryon strain has an 'I1/I5' heteroallelic genotype for the ITS marker, indicating the presence of alleles I1 and I5, which distinguishes it from other known commercial brown strains.

Description of the MFPC-1-ELF Marker:

The 5' end of this marker segment begins at position 1 with the first "G" in the sequence GGGAGGGT, corresponding to H97 JGI V2.0 Scaffold 8 position 829770 (Morin et al. 2012) and extending in a forward orientation (relative to the scaffold orientation) for ca. 860 nt in most alleles. At present, at least 7 alleles incorporating at least 40 polymorphic positions have been documented from diverse strains in Sylvan's breeding collection.

The MFPC-1-ELF marker is derived from a sequence mapped by Marie Foulongne-Oriol et al., "An expanded genetic linkage map of an intervarietal *Agaricus bisporus* var. *bisporus-A. bisporus* var. *burnettii* hybrid based on AFLP, SSR and CAPS markers sheds light on the recombination behaviour of the species." *Fungal Genetics and Biology* 47: 226-236 (2010) that is linked to the PPC-1 locus described by Callac et al., "Evidence for PPC1, a determinant of the pilei-pellis color of *Agaricus bisporus* fruit bodies. *Fungal Genet. Biol.* 23, 181-188 (1998). An equivalent linked marker has been used as described in Loftus et al., "Use of SCAR marker for cap color in *Agaricus bisporus* breeding programs." *Mush. Sci.* 15, 201-205 (2000). While several different primers can be and have been used to amplify segments of DNA in which the MFPC-1-ELF marker is present and from which it can be sequenced, digested, electrophoretically characterized, or otherwise analyzed, the primer sequences employed by the inventors for the development of the disclosed data are: Forward: 5'-aytcrcaamaacataccttcaac-3' (SEQ ID NO. 5); reverse: 5'-cattcggcgattttctca-3' (SEQ ID NO. 6), with 35 PCR cycles, 55C anneal temperature, 0.5 min. extension time.

Alleles present in the J14756-s3/J15051 immediate pedigree, or in commercially cultivated brown strains, include alleles E1, E2, E3, E4, and E6, characterized as follows (using the format: nucleotide base character @ alignment position, based on alignment of 8 alleles):

Allele E1: 'A' @ 63; 'A' @ 77; 'A' @ 232; 'G' @ 301; 'A' @ 309; 'T' @ 334; 'A' @ 390; 'A' @ 400; 'T' @ 446, 'A' @ 481; etc.

Allele E2: 'A' @ 63; 'G' @ 77; 'A' @ 232; 'G' @ 301; 'G' @ 309; 'T' @ 334; 'G' @ 390; 'G' @ 400; 'C' @ 446, 'G' @ 481; etc.

Allele E3: 'A' @ 63; 'A' @ 77; 'A' @ 232; 'G' @ 301; 'G' @ 309; 'T' @ 334; 'A' @ 390; 'A' @ 400; 'C' @ 446, 'G' @ 481; etc.

Allele E4: 'G' @ 63; 'A' @ 77; 'A' @ 232; 'G' @ 301; 'G' @ 309; 'T' @ 334; 'A' @ 390; 'A' @ 400; 'C' @ 446, 'G' @ 481; etc.

Allele E6: 'A' @ 63; 'A' @ 77; 'A' @ 232; 'A' @ 301; 'G' @ 309; 'T' @ 334; 'A' @ 390; 'A' @ 400; 'C' @ 446, 'G' @ 481; etc.

The J14756-s3 homokaryon line carries allele E3. The wild homokaryon line carries allele E4. The J15051 heterokaryon strain has an 'E3/E4' heteroallelic genotype at the MFPC1-ELF marker locus, indicating the presence of alleles E3 and E4, which distinguishes it from the OFB strains, which have an 'E3/E6' genotype and lack allele E4, and also from other strains which are homoallelic and/or which carry other different alleles.

Description of the AN Marker:
The 5' end of this marker segment begins at position 1 with the first "G" in the sequence GGGTTTGT, corresponding to H97 JGI V2.0 Scaffold 9 position 1701712 (Morin et al. 2012) and extending in a forward orientation (relative to the scaffold orientation) for ca. 1660 nt (in the H97 genome) to 1700 nt (in the alignment space) in known alleles; several insertions/deletions have created length polymorphisms which, in addition to point mutations of individual nucleotides, characterize the alleles. At present, 5 alleles incorporating more than 70 polymorphic positions have been documented from diverse strains in Sylvan's breeding collection.

The AN marker was designed from sequences obtained from PCR products produced by the use of primers disclosed by Robles et al., U.S. Pat. No. 7,608,760, and/or from contiguous or overlapping genome sequences, to improve upon the performance, reliability, and consistency of results, as compared to the markers as originally described; they are genotypically and genomically equivalent. While several different primers can be and have been used to amplify segments of DNA in which the AN marker is present and from which it can be sequenced, digested, electrophoretically characterized, or otherwise analyzed, the primer sequences employed by the inventors for the development of the disclosed data for AN are: Forward: 5'-gacgatgcgggactggtggat-3' (SEQ ID NO. 7); Reverse: 5'-ggtctggcctacrggagtgttgt-3' (SEQ ID NO. 8), with 35 PCR cycles, 64C anneal temperature, 2 min. extension time.

Alleles present in the J14756-s3/J15051 immediate pedigree, or in commercially cultivated brown strains, include alleles N1, N2, N3, N4, and N7, characterized in part as follows (using the format: nucleotide base character @ alignment position, based on alignment of alleles N1 through N5):

Allele N1: 'G' @ 640; [deletion] @ 844-846; 'C' @ 954; 'T' @ 882; 'A' @ 994, etc.

Allele N2: 'A' @ 640; [deletion] @ 844-846; 'C' @ 954; 'T' @ 882; 'A' @ 994, etc.

Allele N3: 'A' @ 640; [deletion] @ 844-846; 'T' @ 954; 'C' @ 882; 'C' @ 994, etc.

Allele N4: 'A' @ 640; [deletion] @ 844-846; 'C' @ 954; 'C' @ 882; 'G' @ 994, etc.

Allele N7: differs from allele N5 in lacking a unique 'G' @ 449, a unique 'T' @ 537, and a unique 'GT' @ 590-591.

The J14756-s3 homokaryon line carries allele N4. The wild homokaryon line carries allele N3. The J15051 heterokaryon strain has an 'N3/N4' heteroallelic genotype at the AN marker locus, indicating the presence of alleles N3 and N4, which distinguishes it from the OFB strains, which have an 'N4/N4' genotype and lack allele N3, and from other strains which are homoallelic and/or which carry alleles N1 or N2 or other different alleles.

Description of the AS Marker:
The 5' end of this marker segment begins at position 1 with the first "G" in the sequence GG(T/N)GNGAT, corresponding to H97 JGI V2.0 Scaffold 4 position 752867 (Morin et al. 2012) and extending in a forward orientation (relative to the scaffold orientation) for ca. 1620 nt (in the H97 genome) to 1693 nt (in the alignment space) in known alleles; several insertions/deletions have created length polymorphisms which, in addition to point mutations of individual nucleotides, characterize the alleles. At present, 7 alleles incorporating more than 80 polymorphic positions have been documented from diverse strains in Sylvan's breeding collection.

The AS marker, like the AN marker, was designed from sequences obtained from PCR products produced by the use of primers disclosed by Robles et al., U.S. Pat. No. 7,608,760, and/or from contiguous or overlapping genome sequences, to improve upon the performance, reliability, and consistency of results, as compared to the markers as originally described; they are genotypically and genomically equivalent. While several different primers can be and have been used to amplify segments of DNA in which the AS is present and from which it can be sequenced, digested, electrophoretically characterized, or otherwise analyzed, the primer sequences employed by the inventors for the development of the disclosed data for AS are: Forward: 5'-ccgccagcacaaggaatcaaatg-3' (SEQ ID NO. 9); Reverse: 5'-tcagtcggccctcaaaacagtcg-3' (SEQ ID NO. 10), with 35 PCR cycles, 64C anneal temperature, 2 min. extension time.

Alleles present in the J14756-s3/J15051 immediate pedigree, or in commercially cultivated brown strains, include alleles SA, AB, SC and SD, characterized in part as follows (using the format: nucleotide base character @ alignment position, based on alignment of alleles SA through SG):

Allele SA: 'C' @ 28; 'A' @ 153; [deletion] @ 258-263; 'G' @ 275; 'C' @ 281; [insertion]+'TTTCCCAGC'+[insertion] @ 309-349; 'C' @ 404, etc.

Allele SB: 'C' @ 28; 'A' @ 153; [deletion] @ 258-263; 'T' @ 275; 'G' @ 281; [insertion]+'TTTCCCAGC'[insertion] @ 309-349; 'C' @ 404, etc.

Allele SC: 'T' @ 28; 'A' @ 153; 'GATATC' @ 258-263; 'G' @ 275; 'T' @ 281; [insertion]+'TTTCTCAGC'[insertion] @ 309-349; 'C' @ 404, etc.

Allele SD: 'C' @ 28; 'C' @ 153; [deletion] @ 258-263; 'T' @ 275; 'C' @ 281; [deletion] @ 309-349; 'T' @ 404, etc.

The J14756-s3 homokaryon line carries allele SD. The wild homokaryon line carries allele SA. The B15051-s3 heterokaryon has an 'SA/SD' heteroallelic genotype at the AS marker locus, indicating the presence of alleles SA and SD, which distinguishes it from the OFB lineage group strains, which have an 'SC/SD' genotype, and also from other strains which are homoallelic and/or which carry allele SB, SC or other different alleles.

Description of the FF Marker:
The 5' end of this marker segment begins at position 1 with the first "T" in the sequence TTCGGGTG, corresponding to H97 JGI V2.0 Scaffold 12 position 281674 (Morin et al. 2012) and extending in a forward orientation (relative to the scaffold orientation) for ca. 570 nt in most alleles. At present, 7 alleles incorporating at least 20 polymorphic positions have been documented from diverse strains in Sylvan's breeding collection.

The FF marker, like the AN and AS markers, was designed from sequences obtained from PCR products produced by the use of primers disclosed by Robles et al., U.S. Pat. No. 7,608,760, and/or from contiguous or overlapping genome sequences, to improve upon the performance, reliability, and consistency of results, as compared to the markers as originally described; they are genotypically and genomically equivalent. While several different primers can be and have been used to amplify segments of DNA in which the FF marker is present and from which it can be sequenced, digested, electrophoretically characterized, or otherwise analyzed, the primer sequences employed by the inventors for the development of the disclosed data for FF are: Forward: 5'-tcgggtggttgcaactgaaaag-3' (SEQ ID NO. 11); Reverse: 5'-ttccttccgccttaattgtttct-3' (SEQ ID NO. 12), with 35 PCR cycles, 64C anneal temperature, 2 min. extension time.

Alleles present in the J15051 immediate pedigree, or in commercially cultivated brown strains, include alleles FF1, FF2, FF3, FF4, and FF7, characterized as follows (using the format: nucleotide base character @ alignment position, based on alignment of alleles 1 and 2):

Allele FF1: 'CCG' @ 48-50; 'A' @ 64; 'C' @ 91;
Allele FF2: 'TTC' @ 48-50; 'A' @ 64; 'C' @ 91
Allele FF3: 'TTC' @ 48-50; 'A' @ 64; 'T' @ 91
Allele FF4: 'TTC' @ 48-50; 'A' @ 64; 'A' @ 91
Allele FF7: 'TTC' @ 48-50; 'G' @ 64; 'T' @ 91

The J14756-s3 homokaryon line carries allele FF2. The wild homokaryon line carries allele FF2. The J15051 heterokaryon strain has a homoallelic 'FF2/FF2' genotype at the FF marker locus, indicating the presence of two copies of allele FF2. This distinguishes B15051 from the OFB strains, which have an 'FF1/FF2' genotype, and also from many other strains which carry alleles other than FF2.

In aggregate, the composite genotype of line J14756-s3, and of strain J15051, are each novel and distinct from all other strain genotypes known.

The genotype data for six additional marker loci in standard use as discussed above are provided in Table II.

tion, or, in the case of PTA-6877, in the development of commercial cultivar strains. Match percentage in Table II calculates the proportion of genotypic identity between strain J15051 and each of the other strains at these six loci, providing a simple demonstration of genotypic novelty in J15051, demonstrating that other strains known in the art do not approach even 75% genotypic identity with the novel genotype of strain J15051. The genotype of J14756-s3 incorporates, for example, a novel allele, I5, at the ITS marker locus, and in combination with the genotype of the second line that was mated with line J14756-s3, produces the combined genotype of strain J15051 with an ITS marker genotype of I1/I5.

Line J14756-s3 can be identified, and the presence of its genome in all lines derived from it and in descendent F1 hybrids including J15051 verified, through its molecular genetic marker profile as shown in Tables I and II. A culture or product incorporating the genetic marker profile shown for J14756-s3 in Tables I and II is an embodiment of the invention. Another embodiment of this invention is an *Agaricus bisporus* line or its parts comprising the same alleles as the line J14756-s3 for at least 75% of the loci listed in Tables I and II. In other embodiments, this line or its parts comprises the same alleles as the line J14756-s3 for at least 80%, 85%, 90%, 95%, 96%, 97%, 98%, 99% or essentially 100% of the loci listed in Tables I and II.

A cell comprising the same alleles as a cell of line J14756-s3 for at least 75% of the loci listed in Tables I and II is also an embodiment of this invention. In other embodiments, cells comprising the same alleles as a cell of line J14756-s3 for at least 80%, 85%, 90%, 95%, 96%, 97%, 98%, 99% or essentially 100% of the loci listed in Tables I and II, are provided. Also encompassed within the scope of the invention are cultures substantially benefiting from the use of line J14756-s3 in their development, such as hybrid offspring having line J14756-s3 as a parent, grandparent, great-grandparent, great-great-grandparent, etc., and lines derived from J14756-s3, including lines having a trait introduced through at least one technique selected from the group of techniques comprising: introgressive matings of offspring back to line J14756-s3, mutagenesis, somatic selection, and transformation. Similarly, an embodiment of this invention is an *Agaricus bisporus* heterokaryon comprising at least

TABLE II

| | Markers: | | | | | | |
|---|---|---|---|---|---|---|---|
| Strain: | p1n150/Mat | MFPC-1-ELF | FF | AN | AS | ITS | Match % |
| J15051 | 2/5 | E3/E4 | FF2/FF2 | N3/N4 | SA/SD | I1/I5 | [100%] |
| B14528 | 2/5 | E3/E4 | FF1/FF3 | N3/N4 | SC/SD | I1/I2 | 66.7% |
| 28c, [Heirloom] | 1T/5 | E3/E4 | FF1/FF3 | N2/N3 | SA/SD | I1/I1 | 58.3% |
| 28b, [Braun] | 1T/5 | E3/E4 | FF1/FF4 | N2/N3 | SB/SD | I1/I1 | 50.0% |
| PTA-6877 | 1T/2 | E2/E3 | FF1/FF1 | N2/N4 | SD/SD | I1/I2 | 33.3% |
| S600 | 1T/2 | E1/E3 | FF2/FF2 | N2/N4 | SC/SD | I1/I2 | 41.7% |
| J10263 | 1T/2 | E1/E3 | FF2/FF7 | N4/N7 | SC/SD | I1/I2 | 50.0% |
| OFB lineage group | 1T/3 | E3/E6 | FF1/FF2 | N4/N4 | SC/SD | I1/I3 | 41.7% |
| J14756-s3 | 2 | E3 | FF2 | N4 | SD | I5 | |
| wild line | 5 | E4 | FF2 | N3 | SA | I1 | |

It will be appreciated that strains B14528, Heirloom, Brawn, PTA-6877, S600, J10263, and the Old-Fashioned Brown (=OFB) lineage which includes strains 2400, Bs526, SB-65, SB-295, 800, 805, and RWK 2042, among many others, are brown-capped strains that have either a past history or a contemporary presence in commercial cultivation, or, in the case of PTA-6877, in the development of one allele per locus that is the same allele as is present in the J14756-s3 line for at least 75% of the marker loci listed in Tables I and II. In other embodiments, heterokaryons comprising at least one allele per locus that is the same allele as is present in the J14756-s3 line for at least 80%, 85%, 90%, 95%, 96%, 97%, 98%, 99% or essentially 100% of the marker loci listed in Tables I and II, are provided. More particularly, the heterokaryon may be a hybrid descendent of line J14756-s3.

In accordance with the above, one or more embodiments of this invention include a line J14756-s3 progeny mushroom culture, culture part, mushroom, or mushroom part that is a first-generation (F1) heterokaryotic hybrid mushroom culture comprising two sets of alleles, wherein one set of alleles is the same as line J14756-s3 at all of the marker loci listed in Table I. A mushroom cell or hyphal element wherein one set of the alleles is the same as line J14756-53 at all of the marker loci listed in Table I is also an embodiment of the invention. This mushroom cell or hyphal element may be a part of a culture, a commercial inoculum or 'spawn' product, a mushroom, or a part of a mushroom produced by mating line J14756-s3 with another mushroom culture. Further embodiments of this invention may include an essentially derived variety of the F1 hybrid, produced by inter-tetrad or intra-tetrad selfing of the F1 hybrid, or by modification of the F1 culture, and more specifically by somatic selection, tissue culture selection, single spore germination, multiple spore germination, selfing, repeated mating back to the initial culture, mutagenesis, and transformation.

Line J14756-s3 and its presence in cultures, culture parts, hybrids, mushrooms and mushroom pieces and parts can be identified through a molecular marker profile. A mushroom culture cell or hyphal element having the marker profile shown in Table I is an embodiment of the invention. Such a mushroom cell or hyphal element may be heterokaryotic.

Line J14756-s3 represents a new base genetic line into which a new locus or trait may be introgressed. Direct transformation and inbreeding represent two useful methods that can be applied to accomplish such an introgression. Introgression producing a trait conversion comprises the step of mating line J14756-s3 to a second strain, and then mating progeny of that mating with line J14756-s3, repetitively, until a derived variant of line J14756-s3 incorporating an introduced gene determining a novel trait is obtained. Strains and lines produced by this method may have, for example, in the range of 75, 80, 85, 90, 95, 96, 97, 98, 99, or 99.9% of the DNA of line J14756-s3, and are therefore Essentially Derived Varieties of line J14756-s3, and are an embodiment of the invention.

Line J14756-s3 can be used to produce hybrid cultures with desirable productivity, timing, appearance, and other agronomic traits as is required of successful commercial mushroom strains, while also providing more diversified, novel non-cultivar germplasm. Line J14756-s3 has been found to have an advantageous genotype for mating to produce commercially useful hybrid strains, an attribute that was determined empirically after the fact, but which could not be predicted successfully using any existing known method.

In order to demonstrate practice of the present invention, the line J14756-s3 was compared to other lines. J14756-s3 is a line selected from among haploid progeny of a 6th generation in a hybrid pedigree initiated by Sylvan America, Inc. in 1993. This line, within a suitable heterokaryotic genetic background, dominantly confers a brown cap color trait upon heterokaryotic offspring; cap color is determined primarily by alleles at the Ppc-1 locus on Chromosome 8. Line J14756-s3 has the Mat-2 mating type genotype and behavioral phenotype (whereas lines obtained from the traditional Old Fashioned Brown lineage group of strains always have a Mat-1 mating type; the Mat-3 allele is also present in those OFB parent strains but is never found in viable offspring lines). The presence of the Mat-2 allele confers a particular sexual compatibility that is uncommon for a brown breeding line and thus usefully allows for different combinations of lines to be mated together, for example the Mat-1 OFB lines can be mated to J14756-s3. The unique genotype of line J14756-s3 also contributes to and supports several commercially desirable traits in hybrid offspring, including crop timing and productivity, and mushroom size, appearance and general retail appeal. Because line J14756-s3 is a haploid line, it is incapable of producing a crop of mushrooms, and consequently no "J14756-s3 mushroom" is obtainable and no direct characterization of a crop or product phenotype is possible. Therefore most selection criteria applied to haploid lines including line J14756-s3 are determined empirically by evaluating a series of matings which share a common parent such as line J14756-s3. In effect, this 'combining ability', i.e., the ability to mate and produce a useful proportion of interesting and useful novel hybrids in strain development programs, is applied using empirical testing and comprehensive evaluation criteria as is well known in the art. Line J14756-s3 is among the top-ranked haploid lines discovered from among its cohort of sibling lines. No previous hybrid, prior to creation of hybrids using line J14756-s3, had the particular combination of desirable traits (including specific details of its cap color, harvest yield, and cropping schedule, plus a particular novel incompatibility phenotype) seen among hybrids incorporating line J14756-s3. No previous line has ever been observed to produce the combinations of desirable traits (including specific details of its cap color, harvest yield, and cropping schedule, plus a particular novel incompatibility phenotype) observed among hybrids incorporating line J14756-s3.

As previously discussed, the results in Table I compare a specific F1 hybrid mushroom culture strain, namely a strain designated J15051, which has been deposited with the NRRL as Accession No. 67316, for which line J14756-s3 is a parent with other hybrids. The results presented herein show that homokaryotic line J14756-s3 shows good combining ability.

A single mushroom hybrid results from the mating of two haploid, homoallelic lines, each of which has a genotype that complements the genotype of the other at the mating type locus MAT. The hybrid progeny in the first generation is designated F1. F1 hybrids may be useful as new commercial varieties for mushroom production, or as starting material for the production of inbred offspring and/or EDVs, or as parents of the next generation of haploid lines for producing subsequent hybrid strains in an F2 or later generation, such as F3, F4, F5, and so forth into F10 and beyond.

Line J14756-s3 may be used to produce hybrid mushroom cultures, including F1 hybrids and their descendents in generations F2, F3, F4, F5, F6, F7, F8 and subsequently, even to F10 and beyond. One such embodiment is the method of mating homokaryotic line J14756-s3 with another homokaryotic mushroom line, to produce a first generation F1 hybrid culture. The first generation culture, culture part, mushroom, and mushroom piece or part produced by this method is an embodiment of the invention. The first generation F1 culture will comprise a complete set of the alleles of the homokaryotic line J14756-s3. The strain developer can use either strain development records or molecular methods to identify a particular F1 hybrid culture produced using line J14756-s3. Further, the strain developer may also produce F1 hybrids using lines which are EDVs of J14756-s3, including 'narrow modifications' such as transgenic or introgressive trait conversions and mutagenized and somatically selected cultures obtained from line J14756-s3. Another embodiment is the method of mating line J14756-s3, or a narrowly modified version of that line (i.e., an EDV), with a different, heterokaryotic culture of *Agaricus bisporus*. This latter method is less efficient than mating using two homokaryotic lines, but can also result in the production of novel hybrid cultures. Additionally, an EDV of any culture of the invention is also an embodiment of the invention.

The development of a mushroom hybrid in a typical mushroom strain development program involves many or all of the following steps: (1) the obtaining of strains or stocks from various germ plasm pools of the mushroom species for initial matings; (2) matings between pairs of pure cultures on sterile microbiological growth media such as potato dextrose agar (PDA); (3) the obtaining and use of promising hybrid strains from matings to produce subsequent generations of homokaryotic progeny lines, such as line J14756-s3, which are individually uniform; (4) the use of those lines in matings with other lines or strains to produce a subsequent hybrid generation; (5) repetition of steps (2-4) as needed; (6) obtaining of pre-commercial hybrid strains and, optionally, the use of essential derivation techniques such as selfing to produce a final commercial strain. In one embodiment, the repetition of steps (2-4) may be performed up to 5 times. In various other embodiments, steps (2) to (4) may be repeated anywhere from 0 up to 1, 2, 3, 4, 5, 6, 7, 8, 9 or 10 times. The homokaryotic lines are not reproductively competent ('fertile'). Fertility, the ability to produce a crop of mushrooms, is restored in complementary matings with other haploid, or less commonly, heterokaryotic strains. An important consequence of the homoallelism and homogeneity of the homokaryotic line is that the hybrid between a defined pair of homokaryotic lines may be recreated indefinitely as long as the homokaryotic lines are preserved and/or propagated. In a mating attempt between a homokaryotic line and a heterokaryon, in the absence of somatic recombination, either or both of only two possible defined novel heterokaryotic genotypes may be obtained, each of which will incorporate line J14756-s3.

Using line J14756-s3, specific application with repetition of the steps described above can produce any pedigree structure from any arrangement of stocks, lines and hybrids within that structure. A hybrid of the F1, F2, F3, F4, F5, F6, F7, F8, F9, F10 or any subsequent hybrid generation can be produced from line J14756-s3 using steps 1-6 described above.

Although the invention has been described in terms of particular embodiments in this application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

The utility of the culture of homokaryotic line J14756-s3 can be demonstrated with reference to one of its earliest F1 hybrid descendents, J15051, which has been studied extensively to provide the following examples.

Under commercial conditions, J15051 can produce a crop of mushrooms that can be harvested beginning on the same day as crops of strains BR06/"Heirloom" and B14528/"Tuscan", which are two leading commercial brown strains, as shown in Table III.

TABLE III

Days after casing application until first and last harvest of first break crop

| Test ID | Date | | J15051 | Heirloom | Tuscan |
|---|---|---|---|---|---|
| 14-234 | July 2014 | 1st day pick | 14 | 14 | 14 |
| | | Last day 1st bk | 16 | 16 | 16 |
| 14-299 | August 2014 | 1st day pick | 14 | 14 | |
| | | Last day 1st bk | 16 | 16 | |
| 14-329 | September 2014 | 1st day pick | 14 | 14 | |
| | | Last day 1st bk | 16 | 16 | |
| 16-243 | October 2016 | 1st day pick | 15 | 15 | 15 |
| | | Last day 1st bk | 16.3 | 16 | 17 |

Maintaining a typical two-week casing colonization and development period prior to first day of harvest preserves facility efficiency and ease of labor and task scheduling while ensuring that more of the crop will be harvested at a time when the negative influences of crop diseases and pests are relatively less, supporting both crop yield and product quality. The novel genotype of J14756-s3 confers this advantage upon the F1 hybrid in concert with the genotype of the second haploid nucleus in the F1 heterokaryon.

It will be appreciated that other F1 hybrid strains having line J14756-s3 as a parent, in addition to J15051, have also been produced and can produce a crop of mushrooms that can be harvested beginning on the same day as or before crops of strains Heirloom or its clonal subculture SB-28Cc, or Tuscan. The timing for these crops are set forth in Table IV, wherein a zero value indicates identical crop timing with the control strain and a negative integer indicates the number of days that the F1 hybrid strain entered harvest earlier than the control. The number of F1 hybrids exhibiting this early or on-time harvest indicates that the J14756-s3 line contributes to the expression of this trait in F1 hybrid offspring.

TABLE IV

Timing of harvest compared to control strain

| F1 strain | 1st day of pick | Control |
|---|---|---|
| J15051 | 0 | SB-28c |
| J15057 | 0 | SB-28c |
| J15618 | 0 | SB-28Cc |
| J15619 | 0 | SB-28Cc |
| J15620 | 0 | SB-28Cc |
| J15621 | 0 | SB-28Cc |
| J15622 | 0 | SB-28Cc |
| J15279 | 0 | SB-28Cc |
| J15293 | 0 | SB-28Cc |
| J15300 | 0 | SB-28Cc |
| J15307 | 0 | SB-28Cc |
| J15314 | 0 | SB-28Cc |
| J15380 | 0 | SB-28Cc |
| J15618 | -2 | Tuscan |
| J15619 | -2 | Tuscan |
| J15620 | -2 | Tuscan |
| J15621 | -2 | Tuscan |
| J15622 | -2 | Tuscan |

The crop yields produced by J15051 are in a similar range as, i.e., either (a) not significantly different at a 95% probability level from, or (b) on overall average within at least 95% of, the yields obtained from either of two dark brown commercial control strains, as shown in Table V.

TABLE V

Crop yield of strain J15051 compared to commercial control strains Heirloom and Tuscan.

| Test ID | Date | J15051 Yield | Heirloom Yield | t-test: p value | Statistical Difference | Tuscan Yield | t-test: p value | Statistical Difference |
|---|---|---|---|---|---|---|---|---|
| Facility 1 | | | | | | | | |
| 14-234 | July 2014 | 3.50 | 3.44 | 0.601 | NSD | 4.00 | 0.108 | NSD |
| 14-299 | Aug 2014 | 3.56 | 3.47 | 0.438 | NSD | — | — | — |
| 14-329 | September 2014 | 4.11 | 4.16 | 0.713 | NSD | — | — | — |
| Facility 2 | | | | | | | | |
| 142341 Rm C | October 2014 | 3.77 | 3.86 | 0.676 | NSD | — | — | — |
| 142851 Rm C | 2014 December | 4.57 | 4.10 | 0.078 | NSD | — | — | — |
| 150611 | March 2015 | 4.58 | 4.76 | 0.201 | NSD | — | — | — |
| 151211 | May 2015 | 4.60 | 4.58 | 0.885 | NSD | — | — | — |
| 152137 | September 2015 | 4.00 | 4.06 | 0.595 | NSD | 3.26 | 0.602 | NSD |
| 152645 Rm B | November 2015 | 4.10 | 4.59 | 0.005 | −12% | 3.88 | 0.075 | NSD |
| 160202 Rm D | January 2016 | 6.55 | 5.90 | 0.002 | +11% | 6.18 | 0.001 | +6% |
| 161528 Rm A | July 2016 | 3.94 | 4.19 | 0.349 | NSD | — | — | — |
| Facility 3 | | | | | | | | |
| Test 1 normal | July 2015 | 31434 | 29331 | 0.011 | +7% | | | |
| Test 1 + water | July 2015 | 33455 | 32400 | 0.416 | NSD | | | |

Data in Table V from facility 2 represent 2-flush totals except as noted; data from facilities 1 and 3 represent 3-flush totals. Data from facilities 1 and 2 are presented as lbs. per square foot; data from facility 3 is presented as g per square meter. Statistical significance was determined using a t-test. NSD means No Significant Difference. Heirloom is also known as PTA-6876 and BR06; Tuscan is also known as NRRL 50900 and B14528.

It is uncommon to observe such high productivity in experimental hybrids, of which the Applicant has now evaluated more than 20,000. It is extremely uncommon to observe this trait in an F1 hybrid in conjunction with all of the other requisite traits for commercial acceptance, for example an appealing appearance, and it is even more unusual to observe this yield trait in a strain producing mushrooms having a medium-brown cap color. The unique, novel genotype of J14756-s3 confers this advantage upon the F1 hybrid in concert with the genotype of the second haploid nucleus in the F1 heterokaryon.

It will be appreciated that data for crop yields for other F1 hybrid strains having J14756-S3 as a parent, has also been obtained. The number of F1 hybrid strains having high crop yields in their first test indicates an advantage of good combining ability exhibited by line J14756-s3. The data is presented hereinbelow in Table VI. The control strains SB-28c, SB-28Cc, and SB-28Cd are clonal, genetically identical subcultures of the Heirloom strain.

TABLE VI

Crop Yields for F1 hybrid strains compared to control strains

| F1 strain | Control | Strain Yield | Control Yield | % control Yield |
|---|---|---|---|---|
| J15051 | SB-28c | 4.23 | 4.17 | 101.44 |
| J15057 | SB-28c | 4.3 | 4.17 | 103.12 |
| J15619 | SB-28Cc | 3.72 | 2.99 | 124.41 |
| J15620 | SB-28Cc | 3.67 | 2.99 | 122.74 |
| J15622 | SB-28Cc | 3.84 | 2.99 | 128.43 |
| J15300 | SB-28Cc | 3.19 | 2.97 | 107.41 |
| J15307 | SB-28Cc | 3.28 | 2.97 | 110.44 |
| J15314 | SB-28Cc | 3.09 | 2.97 | 104.04 |
| J15618 | Tuscan | 2.95 | 1.98 | 148.99 |
| J15619 | Tuscan | 3.72 | 1.98 | 187.88 |
| J15620 | Tuscan | 3.67 | 1.98 | 185.35 |
| J15621 | Tuscan | 2.66 | 1.98 | 134.34 |
| J15622 | Tuscan | 3.84 | 1.98 | 193.94 |

The unique, novel genotype of the line J14756-s3 culture also tempers the expression of the brown cap color trait when mated with a second homokaryon that is carrying a brown allele at the PPC-1 color trait determining locus, as shown in Table VII.

TABLE VII

Cap surface color measured as L-value (white light reflectance) by Minolta Chroma Meter, on 30-mushroom samples of strains J15051 and B14528/"Tuscan" grown in identical commercial conditions

| | L-value (Day 1) | | | L-value (Day 2) | | |
|---|---|---|---|---|---|---|
| | Mean | SD | p-value | Mean | SD | p-value |
| Strain: J15051 | 65.03 | 5.09 | 0.0049*** | 66.61 | 4.99 | 0.0283* |
| Control: B14528/"Tuscan" | 61.38 | 4.57 | NA | 64.11 | 3.73 | NA |
| Benchmark: BR06/"Heirloom" | 56.66 | — | — | | | |

Data in Table VII were obtained from mushrooms taken on Day 1 or Day 2 of first break. J15051 was lighter in color (i.e. had a measurably greater L-value or white light reflectance) than B14528/"Tuscan" with a statistical significance greater than 0.005 (***) on Day 1 and greater than 0.05 (*) on Day 2. Benchmark data used to characterize and distinguish BR06/"Heirloom" in U.S. Pat. No. 7,608,768 are provided for comparison. The low reported L-value of 56.66 for BR06 in U.S. Pat. No. 7,608,768 indicates a darker color than what has been recorded for J15051 and for B14528/"Tuscan". Although sample data parameters were not provided in U.S. Pat. No. 7,608,768, a statistically significantly lighter color for J15051 is demonstrated by two facts: (1), even B14528, with an L-value of 61.38 or 64.11, is significantly darker than J15051 by this measure, while the BR06

L-value of 56.66 is darker yet and therefore is likely to differ even more significantly, and (2) according to U.S. Pat. No. 7,608,768, a sample set from strain 2400 having a mean L-value score of 60.15 was significantly lighter than BR06 "at the 5% level", i.e., p<=0.05, and therefore the even higher 65.03 and 66.61 L-values recorded for J15051 are likely to be even more significantly different.

In this way the very dark brown cap color of mushrooms obtained from other hybrid strains is avoided. Instead, the J14756-s3 line culture, in such matings, produces an appealing "medium-brown" cap color in a strain that has commercially acceptable performance (timing, yield, etc.) and appearance, which is preferred by some consumers, and which fills a product niche in the retail market that is otherwise vacant at this time.

It will be appreciated that other F1 hybrid strains having J14756-s3 as a parent also provided improved (i.e., a lighter) color.

As shown in Table VIII above, all F1 hybrids for which data was obtained had a cap color in the range of light-brown to medium-brown, which is lighter than the dark-brown control strain SB-28, as tested under subjective color scores (i.e., visual analysis). The control strains SB-28c, SB-28Cc, and SB-28Cd are clonal, genetically identical subcultures of the Heirloom strain, and all produce mushrooms with a dark-brown cap color. It is noted that "insufficient data" in Table VIII means that the photographs needed for color scores either were not recorded in a permanent database, or there was a problem, such as early crop disease, with the test sample that prevented the test data from being gathered.

Vegetative incompatibility (i.e., heterokaryon incompatibility) between J15051 and other brown commercial mushroom strains is present, as shown in Table IX.

TABLE IX

Vegetative incompatibility between strain J15051 and other commercial brown strains, as indicated by first break yield and day of first harvest

| "Strain" on "Strain" | | J15051 on "Strain" | | J15051 on J15051 | | "Strain" on J15051 | |
|---|---|---|---|---|---|---|---|
| SB-295 | SB-295 | J15051 | SB-295 | J15051 | J15051 | SB-295 | J15051 |
| 54 g | 15 d | 0 g | none | 53.3 g | 14 d | 9.3 g | 18 d |
| S-600 | S-600 | J15051 | S-600 | J15051 | J15051 | S-600 | J15051 |
| 35.7 g | 16 d | 0.7 g | 18 d/none | 53.3 g | 14 d | 8.7 g | 18 d |
| Broncoh | Broncoh | J15051 | Broncoh | J15051 | J15051 | Broncoh | J15051 |
| 56.3 g | 16 d | 0.0 g | none | 53.3 g | 14 d | 5.3 g | 18 d |
| J10263 | J10263 | J15051 | J10263 | J15051 | J15051 | J10263 | J15051 |
| 25.7 g | 16 d | 4.3 g | 18 d | 43.3 g | 14 d | 7.3 g | 18 d/none |
| Heirloom | Heirloom | J15051 | Heirloom | J15051 | J15051 | Heirloom | J15051 |
| 45.7 g | 16 d | 2.3 g | 18 d | 43.3 g | 14 d | 7.7 g | 18 d |
| Tuscan | Tuscan | J15051 | Tuscan | J15051 | J15051 | Tuscan | J15051 |
| 55 g | 15 d | 0.0 g | none | 43.3 g | 14 d | 1.7 g | 18 d/none |

TABLE VIII

Cap Color testing under visual analysis

| F1 strain | Test # | Control | Color Notes |
|---|---|---|---|
| J15045 | 13-262 | SB-28c | medium-brown |
| J15051 | 13-262 | SB-28c | medium-brown |
| J15057 | 13-262 | SB-28c | medium-brown |
| J15063 | 13-262 | SB-28c | insufficient data |
| J15618 | 14-202 | SB-28Cc | light-brown |
| J15619 | 14-202 | SB-28Cc | light-brown |
| J15620 | 14-202 | SB-28Cc | medium-brown |
| J15621 | 14-202 | SB-28Cc | medium-brown |
| J15622 | 14-202 | SB-28Cc | medium-brown |
| J15279 | 14-39 | SB-28Cc | light-brown |
| J15286 | 14-39 | SB-28Cc | light-brown |
| J15293 | 14-39 | SB-28Cc | medium-brown |
| J15300 | 14-39 | SB-28Cc | medium-brown |
| J15307 | 14-39 | SB-28Cc | medium-brown |
| J15314 | 14-39 | SB-28Cc | light-brown |
| J15321 | 14-39 | SB-28Cc | medium-brown |
| J15328 | 14-39 | SB-28Cc | insufficient data |
| J15335 | 14-92 | SB-28Cc | insufficient data |
| J15344 | 14-92 | SB-28Cc | insufficient data |
| J15353 | 14-92 | SB-28Cc | insufficient data |
| J15362 | 14-92 | SB-28Cc | insufficient data |
| J15371 | 14-92 | SB-28Cc | medium-brown |
| J15380 | 14-92 | SB-28Cc | light-brown |
| J16550 | 15-184 | SB-28Cd | insufficient data |
| J16562 | 15-184 | SB-28Cd | insufficient data |
| J16604 | 15-241 | SB-28Cd | insufficient data |
| J16620 | 15-241 | SB-28Cd | insufficient data |
| J16636 | 15-241 | SB-28Cd | insufficient data |

Strain J15051 was tested against six other commercial brown strains. Four configurations were compared for each pair of strains: "Strain" on "Strain", "Strain" on J15051, J15051 on J15051, and J15051 on "Strain". "Strain" was always one of the six other commercial brown strains. In each test, a first strain was inoculated into compost and 18 days later the same strain or a different strain was inoculated into the casing layer placed on top of the compost. For each configuration and test, three replicates were made. Yield data for each configuration is the average of three replicates, including all data from the first five days of harvest in the test room, shown in grams (g). As shown, yield was always several times greater from the Self-Self configurations than from the Self-Nonself configurations. First day of harvest was in the interval of day (d) 14 through 18 after casing was applied, if there was no pick during that interval the word "none" appears. Self-Self configurations always began to harvest on days 14 through 16, whereas in Self-Nonself configurations, if there was any harvest at all it did not begin until day 18. Reduced yield and delayed harvest are known in the art to be diagnostic for configurations in which two vegetatively incompatible strains are placed together. The data show that all strains behaved normally in Self-Self configurations, but that J15051 was not compatible with any of the other six strains in Table VI; rather it was incompatible with all of them.

As discussed above, this incompatibility is beneficial to farm hygiene efforts, particularly in programs of crop rotation to reduce and/or eliminate reservoirs of virus diseases of the mushroom crop. The unique, novel genotype of J14756- s3 confers this advantage upon the F1 hybrid in concert with the genotype of the second haploid nucleus in the F1 heterokaryon.

Finally, the genetic novelty introduced into breeding pedigrees and novel lines and strains by J14756-s3, as demonstrated by Tables 1 and 2 and also by the unique incompatibility phenotype, is itself valuable. Genetic novelty and diversity have been known to increase crop resilience and food security at the industry-wide scale. It also provides the consumer with improved chances of finding a product with an individually preferred flavor. All of these potentialities are of benefit to both producers and consumers.

Wild line BP1-s53 may be used in various aspects of this invention, including as the second line for mating with line J14756-s3 to produce strain J15051. As such, a deposit of a culture of wild line BP1-s53 has been made by Sylvan, Inc. d/b/a Sylvan Biosciences, 198 Nolte Dr., Kittanning, Pa. 16201 USA, with the Agricultural Research Services Culture Collection (NRRL), 1815 North University Street, Peoria, Ill. 61604 USA. The date of deposit was Nov. 29, 2016. The culture deposited was taken from the same culture maintained by Sylvan America, Inc., Kittanning, Pa., the assignee, since prior to the filing date of this application, and the inventors and assignee have received authorization to refer to this deposited biological material in any and all patent applications. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 67343. The deposit will be maintained in the depository for a period of 30 years, or 5 years after the last request, or for the effective life of the patent, whichever is longer, and will be replaced as necessary during that period. The culture will be irrevocably and without restriction or condition released to the public upon the filing of the patent application or upon the issuance of a patent, whichever is required by the applicable patent laws.

Although the invention has been described in terms of particular embodiments in this application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

What is claimed is:

1. An *Agaricus bisporus* culture comprising:
at least one set of chromosomes of an *Agaricus bisporus* line J14756-s3, a culture of the line J14756-s3 having been deposited under the NRRL Accession Number 67317, wherein said chromosomes comprise all alleles reported for the line J14756-s3 at the sequence-characterized marker loci listed in at least one of Tables I and II, wherein Table I is provided as follows:

TABLE I

| Scaffold [H97 V2.0 ref. coordinates] | Position of SNP | Cultures: H97 | Wild Line |
|---|---|---|---|
| 1 | 99995 | CTACATTGA | CTACGTTGA |
| 1 | 349966 | AAGGTGGTT | AAGGCGGTT |
| 1 | 600059 | TTTTTTTT- | TTTTTTTTC |
| 1 | 850014 | CCTTTTCAC TCTTGTCAC | TCTTGTCACTCTTGTCAC |
| 1 | 1099971 | GTCGACACC | GTCGACACC |
| 1 | 1350278 | GGAGAGTCG | GGAGAGTCG |
| 1 | 1599956 | AATAAGCGC | AATAAGCGC |
| 1 | 1850032 | CGAGTAATT | CGAGCAATT |
| 1 | 2119049 | ACAATCCAA | ACAACTCAA |
| 1 | 2400243 | ACTTCATGA | ACTTGATGA |
| 1 | 2612870 | AATAGGAGT | AATAGGAGT |
| 1 | 2858975 | GCCGTTCTTGCCGCTCTTG | CCGCTCTTGCCGCTCTT |
| 1 | 2804522 | GAAGACGAC | GAAGGCGAC |
| 1 | 3047987 | AAGGGGGGG | AAGGAGGGG |
| 1 | 3212182 | CACTACGTG | CACTGCGTG |
| 1 | 3256057 | TATCTGTTT TATCCGTTT TATCCGTTT | TATCCGTTT TATCCGTTT |
| 2 | 101820 | ATTAAAGAT | ATTAAAGAT |
| 2 | 350156 | TCGGGGGTG | TCGGAGGTG |
| 2 | 600112 | ATGTATACG | ATGTGTACG |
| 2 | 850338 | TGGTGCTAA TGGTGCTAA | TGGTTCTAA TGGTGCTAA |
| 2 | 1099413 | CCTGACTCA | CCTGGCTCA |
| 2 | 1349512 | CTCAGCAGT | CTCAACAGT |
| 2 | 1600085 | CACAATGCC | CACATTGCC |
| 2 | 1901773 | ACTCGAATT | ACTAAAATT |
| 2 | 2150201 | GTCGTAGGT | GTCGAAGGT |
| 2 | 2400281 | TCAAAACCC | TCAACACCC |
| 2 | 2650136 | ATAATTCCTATAAGTCCT | |
| 2 | 2903620 | ACTAAAAGA | ACTAAAAGA |
| 2 | 3048019 | GTCCGCTGC | GTCCGCTGC |
| 3 | 57117 | TATAGCAGT | TATGACAGT |
| 3 | 65650 | GGCGCTTTTGGCGGTTTTG | GCGGTTTTGGCGGTTTT |
| 3 | 119181 | TTTATACTCTTTATACTC | TTATACTCTTTATACTC |
| 3 | 250112 | GCAGGAGAG | GCCGAAGAG |
| 3 | 750000 | GTCCGGCCA | GTCCGGCCA |
| 3 | 750074 | AGTTTTTTC AGTTTTTTC | AGTTATTTC AGTTwTTTC |
| 3 | 1250000 | TTTTTCCGG TTTTTCCGG | TTTTTCCGG TTTTTCCGG |
| 3 | 1250161 | AGTCTCCTT AGTCTCCTT | AGTCCCCTT AGTCyCCTT |
| 3 | 1750000 | ACGCCTGAC | ACGCCTGAC |
| 3 | 1750033 | TTTTTTGCT TTTTTTGCT | TTTTGTGCT TTTTkTGCT |
| 3 | 2250000 | CGTGGCGAT | CGTGGCGAT |
| 3 | 2250027 | TGTATCAAG | TGTGCCAAG |
| 3 | 2520748 | TAATTCCAC | TAATGCCAC |
| 4 | 100004 | GAGTGATAA | GAGTGATAA |
| 4 | 490648 | CGATCGCGT | CGATTGCGT |
| 4 | 598147 | GATCGCACG | GATCAACAG |
| 4 | 852119 | CGAATATTC | CGAATATTC |
| 4 | 1100085 | GATGCCGAA | GATGACGAA |
| 4 | 1350536 | CGAACTCGG | CGAAATCGG |
| 4 | 1599885 | GATACTTGC | GATACTTGC |
| 4 | 1850288 | ATTCGTGTAATTCATGTA TTCGTGTAATTCrTGTA | |

TABLE I-continued

| | | | |
|---|---|---|---|
| 4 | 2100356 | TCAGAGACC | TCAGAGACC |
| 4 | 2284257 | TCTGGACTG | TCTGAACTG |
| 5 | 100211 | TCCTTGAATTCCTGGAAT | |
| 5 | 350872 | GGCGTGCCC | GGCGTGCCC |
| 5 | 599922 | CGTCATTCA | CGTCATTCA |
| 5 | 851262 | TAATTCTCTTAATCGTCTT AATCGTCTTAATCGTCT | |
| 5 | 1099776 | ACATTGACA | ACATCGACA |
| 5 | 1352539 | TTGTGATCCTTGTGATCCT TGTTGTCCTTGTKrTCC | |
| 5 | 1599904 | AACTTCCTT AACTCCCTT | AACTCCCTT AACTCCCTT |
| 5 | 1851458 | AAATAATCC | AAATTCTCC |
| 5 | 2100025 | CCCTTAGTCCCCTTAGTCC CCTCAGTC | |
| 5 | 2278878 | GGTCAAAAA | GGTCAAAAA |
| 6 | 106294 | GCCATCTCG | GCCACCTCG |
| 6 | 350337 | CATTTGGTTCATTCGGTTC ATTTGGTTCATTyGGTT | |
| 6 | 600047 | GGAGCATTT | GGAGTATTT |
| 6 | 849985 | AGTTCAGGA | AGTTCAGGA |
| 6 | 1098535 | CAAAGATTG | CAAAAATTG |
| 6 | 1349453 | TGTCGGTAG | TGTCAATAG |
| 6 | 1600000 | AAACCTGGA | AAACCTGGA |
| 6 | 1764645 | AACCAGATT | AACCGGATT |
| 6 | 2000087 | GATTTTGCGGATTTTGCGG ATTTTGCGGATTTTGCG | |
| 6 | 2252662 | GGGTTGGTA | GGGTCGGTA |
| 7 | 100284 | GAAATTCAG | GAAATTCAG |
| 7 | 350044 | ATATTCTTT ATATCCTTT | ATATTCTTT ATATyCTTT |
| 7 | 600111 | CAATTATTACAATCATTA | |
| 7 | 850246 | TGACGCATA | TGACGCATA |
| 7 | 1100248 | TCACGGAAG | TCACGGAAG |
| 7 | 1350089 | CTTTTCCCC CTTTTCCCCC TTTTCCCC | CTTTTCCCC |
| 7 | 1605047 | ATACTTGGC | ATACTTGAC |
| 7 | 1860993 | GTCAACCGG | GTCATCCGG |
| 7 | 1898793 | TCCGCATAA | TCCGCATAA |
| 7 | 1991505 | TCTACGGTTTCTACGGTTT CTACGTTTCTACGGTT | |
| 8 | 350000 | ATTGACGCG | ATTGGCGCG |
| 8 | 610549 | GAACTTGAT | GAATACGAT |
| 8 | 1100000 | CATACGATC | CATACGATC |
| 8 | 1100546 | GCCCCAGAA | GCCCCAGAA |
| 8 | 1350000 | AGCTTAACA | AGCTTAACA |
| 8 | 1350240 | ACGGGTACT | ACGGATACT |
| 8 | 1600100 | CTGAACCCT | CTGAACCCT |
| 9 | 100105 | CTCAACCGA | CTCAACCGA |
| 9 | 352455 | AGTCCTCCA | AGTCCTCCA |
| 9 | 599950 | TGGTATCCC | TGGTGTCCC |
| 9 | 1010845 | GGGTGGTGA | GGGTGGTGA |
| 9 | 1244202 | GATGAAGAT | GATGAAGAT |
| 9 | 1504476 | TACTGTACC | TACTGTACC |
| 9 | 1656962 | TATCTACTGTATCTACTGT ATCTACTGTATCTACTG | |
| 10 | 100438 | AATTAATTTGATTAATTTA ATTAATTrATTAATTT | |
| 10 | 350030 | GCGGTTCAA | GCGGTTCAA |
| 10 | 600032 | TTACACTGG | TTACACTGG |
| 10 | 850000 | TCGGTCGGA | TCGGTCGGA |
| 10 | 860249 | CCGCAAATT | CCGCGAATT |
| 10 | 1173178 | ATCCCCAAT | ATCCTCAAT |
| 10 | 1303902 | TGATTTACTTGATTTACTT GATTTACTTGATTTACT | |
| 10 | 1490452 | AATCAGATG | AATCAGATG |
| 11 | 101855 | CCAGCCTGT | CCAGTCTGT |
| 11 | 350000 | GTCAGCAAG | GTCAGCAAG |
| 11 | 350025 | GATAAAACA | GATAAAACA |
| 11 | 600000 | ATGGGCGCG | ATGGGAGCG |
| 11 | 929659 | GGAATATCA | GGAAGTTCA |

TABLE I-continued

| | | |
|---|---|---|
| 11 | 1100608 | AGTGGTCTTAGTGGTCTTA GTGATCTTAGTGrTCTT |
| 11 | 1240230 | ACAAGTTTC ACAAGTTTC |
| 12 | 100000 | CCTTCTAGTCCTTCTAGTC CTTCTAGTCCTTCTAGT |
| 12 | 109790 | GTCTGCACC GTCTACACC |
| 12 | 1000000 | CGAGGAGGA CGAGGAGGA |
| 13 | 100697 | ACGTCTTTAACGTCTTTAA CGTCTTTAACGTCTTTA |
| 13 | 370521 | TTTGAGTCATTTGTGTCAT TTGTGTCATTTGTGTCA |
| 13 | 604345 | CTTCAGCAT CTTCAGCAT |
| 13 | 850249 | GGCTAGTAA GGCTAGTAA |
| 14 | 113109 | AGGGAAATA AGGGGAATA |
| 14 | 372086 | CGATCCCTTCGATTCCTTC GATCCCTTCGATyCCTT |
| 14 | 725684 | ATGAGTTCG ATGAGTTTG |
| 15 | 150013 | GTGGCCCGT GTGGACCGT |
| 15 | 449860 | GAATTTCGG GAATTTCGG |
| 16 | 205778 | CAAGGTCTG CAAGATCTG |
| 16 | 400000 | CCTCGGATT CCTCGGATT |
| 16 | 403998 | CCAAGTACG CCAAATACG |
| 17 | 120000 | TATTCTTCA TATTCTTCA TATTCTTCA TATTCTTCA |
| 17 | 134676 | TTGCCCAGC TTGCTCAGC |
| 17 | 338415 | TGAGAAGCC TGAGAAGCC |
| 17 | 449833 | ATCAAACAA ATCAAACAA |
| 18 | 101884 | ATTACGGAC ATTACGGAC |
| 18 | 112940 | GCGGGTGGG GCGGCTGGG |
| 19 | 98520 | GCTATTGGG GCTATTGGG |
| 19 | 98782 | AAAATTGTT AAAAGTGTT |

| Scaffold [H97 V2.0 ref. coordinates] | Position of SNP | Cultures: J14756-s3 J15051 |
|---|---|---|
| 1 | 99995 | CTACGTTGA CTACGTTGA |
| 1 | 349966 | AAGGCGGTT AAGGCGGTT |
| 1 | 600059 | TTTTCTTT- TTTTyTTTT |
| 1 | 850014 | |
| 1 | 1099971 | GTCGGCACC GTCGrCACC |
| 1 | 1350278 | GGAGGTTCG GGAGrkTCG |
| 1 | 1599956 | AATAGGCGC AATArGCGC |
| 1 | 1850032 | CGAGCAATT CGAGCAATT |
| 1 | 2119049 | ACAACTCAA ACAACTCAA |
| 1 | 2400243 | ACTTGATGA ACTTGATGA |
| 1 | 2612870 | AATAAGAGT AATArGAGT |
| 1 | 2858975 | |
| 1 | 2804522 | GAAGGCGAC GAAGGCGAC |
| 1 | 3047987 | AAGGGGGGG AAGGrGGGG |
| 1 | 3212182 | CACTACGTG CACTrCGTG |
| 1 | 3256057 | |
| 2 | 101820 | ATTAAAGAT ATTAAAGAT |
| 2 | 350156 | TCGGGGGTG TCGGrGGTG |
| 2 | 600112 | ATGTATACG ATGTrTACG |
| 2 | 850338 | TGGTkCTAA |
| 2 | 1099413 | CCTGACTCA CCTGrCTCA |
| 2 | 1349512 | CTCAGCAGT CTCArCAGT |
| 2 | 1600085 | CACAATGCC CACAwTGCC |
| 2 | 1901773 | ACTCAAATT ACTmAAATT |
| 2 | 2150201 | GTCGTAGGT GTCGwAGGT |
| 2 | 2400281 | TCAACACCC TCAACACCC |
| 2 | 2650136 | ATAATTCCT ATAAkTCCT |
| 2 | 2903620 | ACTAAAAGA ACTAAAAGA |
| 2 | 3048019 | GTCCGCTGC GTCCGCTGC |
| 3 | 57117 | TATGACAGT TATGACAGT |
| 3 | 65650 | |
| 3 | 119181 | |
| 3 | 250112 | GCAGGAGAG GCmGrAGAG |
| 3 | 750000 | GTCCGGCCA GTCCGGCCA |
| 3 | 750074 | |
| 3 | 1250000 | |
| 3 | 1250161 | |
| 3 | 1750000 | ACGCCTGAC ACGCCTGAC |
| 3 | 1750033 | |
| 3 | 2250000 | CGTGGCGAT CGTGGCGAT |
| 3 | 2250027 | TGTGCCAAG TGTryCAAG |
| 3 | 2520748 | TAATTCCAC TAATkCCAC |
| 4 | 100004 | GAGTGATAA GAGTGATAA |
| 4 | 490648 | CGATCGCGT CGATyGCGT |
| 4 | 598147 | GATCGACAG GATCrACAG |
| 4 | 852119 | CGAATATTC CGAATATTC |
| 4 | 1100085 | GATGCCGAA GATGmCGAA |
| 4 | 1350536 | CGAACTCGG CGAAmTCGG |
| 4 | 1599885 | GATACTTGC GATACTTGC |
| 4 | 1850288 | |
| 4 | 2100356 | TCAGGGACC TCAGrGACC |
| 4 | 2284257 | TCTGAACTG TCTGrACTG |
| 5 | 100211 | TCCTGGAAT TCCTGGAAT |
| 5 | 350872 | GGCGCGCCC GGCGyGCCC |
| 5 | 599922 | CGTCGTTCA CGTCrTTCA |
| 5 | 851262 | |
| 5 | 1099776 | ACATTGACA ACATyGACA |
| 5 | 1352539 | |
| 5 | 1599904 | |
| 5 | 1851458 | AAATTCTCC AAATTCTCC CCCTyAGTC |
| 5 | 2100025 | |
| 5 | 2278878 | AGTCAAAAA rGTCAAAAA |
| 6 | 106294 | GCCATCTCG GCCAyCTCG |
| 6 | 350337 | |
| 6 | 600047 | GGAGCATTT GGAGyATTT |
| 6 | 849985 | AGTTCAGGA AGTTCAGGA |
| 6 | 1098535 | CAAAGATTG CAAArATTG |
| 6 | 1349453 | TGTCGGTAG TGTCrrTAG |
| 6 | 1600000 | AAACCTGGA AAACCTGGA |
| 6 | 1764645 | AACCGGATT AACCrGATT |
| 6 | 2000087 | |
| 6 | 2252662 | GGGTTGGTA GGGTyGGTA |
| 7 | 100284 | GAAACTCAG GAAAyTCAG |
| 7 | 350044 | |
| 7 | 600111 | CAATTATTA CAATyATTA |
| 7 | 850246 | TGACGCATA TGACGCATA |
| 7 | 1100248 | TCACGGAAG TCACrGAAG |
| 7 | 1350089 | |
| 7 | 1605047 | ATACTTGGC ATACTTGrC |
| 7 | 1860993 | GTCAACCGG GTCAwCCGG |
| 7 | 1898793 | TCCGCATAA TCCGCATAA |
| 7 | 1991505 | |
| 8 | 350000 | ATTGGCGCG ATTGGCGCG |
| 8 | 610549 | GAATTTGAT GATwyGAT |
| 8 | 1100000 | CATACGATC CATACGATC |
| 8 | 1100546 | GCCCGAGAA GCCCsAGAA |
| 8 | 1350000 | AGCTTAACA AGCTTAACA |
| 8 | 1350240 | ACGGGTACT ACGGrTACT |
| 8 | 1600100 | CTGAACCCT CTGAACCCT |
| 9 | 100105 | CTCAGCCGA CTCArCCGA |
| 9 | 352455 | AGTCTCCCA AGTCyyCCA |
| 9 | 599950 | TGGTGTCCC TGGTGTCCC |
| 9 | 1010845 | GGGTAGTGA GGGTrGTGA |
| 9 | 1244202 | GATGGAGAT GATGrAGAT |
| 9 | 1504476 | TACTATACC TACTrTACC |
| 9 | 1656962 | |
| 10 | 100438 | |
| 10 | 350030 | GCGGTTCAA GCGGTTCAA |
| 10 | 600032 | TTACACTGG TTACACTGG |
| 10 | 850000 | TCGGTCGGA TCGGTCGGA |
| 10 | 860249 | CCGCAAATT CCGCrAATT |
| 10 | 1173178 | ATCCTCAAT ATCCTCAAT |
| 10 | 1303902 | |
| 10 | 1490452 | AATCAGATG AATCAGATG |

TABLE I-continued

| | | | |
|---|---|---|---|
| 11 | 101855 | CCAGCCTGT | CCAGyCTGT |
| 11 | 350000 | GTCAGCAAG | GTCAGCAAG |
| 11 | 350025 | GATATAACA | GATAwAACA |
| 11 | 600000 | ATGGGAGCG | ATGGGrGCG |
| 11 | 929659 | GGAATATCA | GGAAkwTCA |
| 11 | 1100608 | | |
| 11 | 1240230 | ACAAATTTC | ACAArTTTC |
| 12 | 100000 | | |
| 12 | 109790 | GTCTGCACC | GTCTrCACC |
| 12 | 1000000 | CGAGAAGGA | CGAGrAGGA |
| 13 | 100697 | | |
| 13 | 370521 | | |
| 13 | 604345 | CTTCAGCAT | CTTCAGCAT |
| 13 | 850249 | GGCTAGTAA | GGCTAGTAA |
| 14 | 113109 | AGGGAAATA | AGGGrAATA |
| 14 | 372086 | | |
| 14 | 725684 | ATGAATTCG | ATGArTTyG |
| 15 | 150013 | GTGGCCCGT | GTGGmCCGT |
| 15 | 449860 | GAATTTCGG | GAATTTCGG |
| 16 | 205778 | CAAGATCTG | CAAGATCTG |
| 16 | 400000 | CCTCGGATT | CCTCGGATT |
| 16 | 403998 | CCAAGTACG | CCAArTACG |
| 17 | 120000 | | |
| 17 | 134676 | TTGCCCAGC | TTGCyCAGC |
| 17 | 338415 | TGAGAAGCC | TGAGAAGCC |
| 17 | 449833 | ATCAAACAA | ATCAAACAA |
| 18 | 101884 | ATTACGGAC | ATTACGGAC |
| 18 | 112940 | GCGGGTGGG | GCGGsTGGG |
| 19 | 98520 | GCTATTGGG | GCTATTGGG |
| 19 | 98782 | AAAATTGTT | AAAAkTGTT | and wherein Table II is provided as follows:

TABLE II

| Strain: | p1n150/ Mat | MFPC-1-ELF | FF | AN | AS | ITS | Match % |
|---|---|---|---|---|---|---|---|
| J15051 | 2/5 | E3/E4 | FF2/ FF2 | N3/ N4 | SA/ SD | I1/ I5 | [100%] |
| B14528 | 2/5 | E3/E4 | FF1/ FF3 | N3/ N4 | SC/ SD | I1/ I2 | 66.7% |
| 28c, [Heirloom] | 1T/5 | E3/E4 | FF1/ FF3 | N2/ N3 | SA/ SD | I1/ I1 | 58.3% |
| 28b, [Braun] | 1T/5 | E3/E4 | FF1/ FF4 | N2/ N3 | SB/ SD | I1/ I1 | 50.0% |
| PTA-6877 | 1T/2 | E2/E3 | FF1/ FF1 | N2/ N4 | SD/ SD | I1/ I2 | 33.3% |
| S600 | 1T/2 | E1/E3 | FF2/ FF2 | N2/ N4 | SC/ SD | I1/ I2 | 41.7% |
| J10263 | 1T/2 | E1/E3 | FF2/ FF7 | N4/ N7 | SC/ SD | I1/ I2 | 50.0% |
| OFB_lineage group | 1T/3 | E3/E6 | FF1/ FF2 | N4/ N4 | SC/ SD | I1/ I3 | 41.7% |
| J14756-s3 | 2 | E3 | FF2 | N4 | SD | I5 | |
| wild line | 5 | E4 | FF2 | N3 | SA | I1. | |

2. The *Agaricus bisporus* culture of claim 1, wherein said culture is an F1 hybrid mushroom culture produced by mating a culture of the line J14756-s3 with a different *Agaricus bisporus* culture.

3. The *Agaricus bisporus* culture of claim 2, wherein said F1 hybrid mushroom culture is vegetatively incompatible with all strains selected from the group consisting of Old Fashioned Brown strains, SB-65, SB-295, 2400, S-600/X618, BR06/"Heirloom", B14528/"Tuscan", Broncoh, and J10263/"Forestiere".

4. An Essentially Derived Variety culture derived from an initial culture which is the culture of claim 1, wherein the Essentially Derived Variety culture has at least 75% genotypic and genomic identity with the culture of the line J14756-s3.

5. A part of the culture of claim 1 selected from the group consisting of hyphae and cells.

6. A product comprising the *Agaricus bisporus* culture of claim 1, wherein the product is selected from the group consisting of mycelium, spawn, inoculum, casing inoculum, fresh mushrooms, processed mushrooms, mushroom pieces, and colonized substrates including grain, compost, and friable particulate matter.

7. A method for developing a resultant culture in a mushroom strain development program comprising:
applying at least one mushroom strain development technique to a first mushroom culture, or parts thereof, wherein said first mushroom culture is a culture comprising at least one set of chromosomes of *Agaricus bisporus* line J14756-s3, wherein a culture of said line J14756-s3 having been deposited under the NRRL Accession Number 67317, to provide the second culture.

8. The method for developing the resultant culture in the mushroom strain development program of claim 7, wherein mushroom strain development techniques are selected from the group consisting of inbreeding, outbreeding, selfing, backcrossing, introgressive trait conversion, essential derivation, somatic selection, single-spore selection, multispore selection, pedigree-assisted breeding, marker assisted selection, mutagenesis and transformation.

9. A method of producing a hybrid mushroom culture comprising:
(a) growing a progeny culture produced by mating the culture of claim 1 with a second *Agaricus bisporus* culture;
(b) mating the progeny culture with a different culture or with itself via at least one offspring line to produce a progeny culture of a subsequent generation;
(c) growing a progeny culture of a subsequent generation and mating the progeny culture of a subsequent generation with itself or a different culture; and
(d) repeating steps (b) and (c) for an additional 0-5 generations to produce a mushroom culture.

10. A cell of the *Agaricus bisporus* culture of claim 1, further comprising a marker profile in accordance with the profile of line J14756-s3 shown in Table I.

11. A process for introducing a desired trait into a culture of *Agaricus bisporus* line J14756-s3 comprising the steps of:
(a) physically mating the culture of *Agaricus bisporus* line J14756-s3, wherein a culture of said line J14756-s3 has been deposited under the NRRL Accession Number 67317, to a second culture of *Agaricus bisporus* having the desired trait, to produce a hybrid;
(b) obtaining an offspring of the hybrid that carries at least one gene that determines the desired trait from the hybrid;

(c) mating said offspring of the hybrid with the culture of *Agaricus bisporus* line J14756-s3 to produce a new hybrid;
(d) repeating steps (b) and (c) at least once to produce a subsequent hybrid;

(e) obtaining a homokaryotic line carrying at least one gene that determines the desired trait and comprising at least 75% of the alleles of line J14756-s3, at sequence-characterized marker loci described in at least one of Tables I and II, wherein Table I is provided as follows:

TABLE I

| Scaffold [H97 V2.0 ref. coordinates] | Position of SNP | Cultures: H97 | Wild Line | J14756-s3 | J15051 |
|---|---|---|---|---|---|
| 1 | 99995 | CTACATTGA | CTACGTTGA | CTACGTTGA | CTACGTTGA |
| 1 | 349966 | AAGGTGGTT | AAGGCGGTT | AAGGCGGTT | AAGGCGGTT |
| 1 | 600059 | TTTTTTTT- | TTTTTTTTC | TTTTCTTT- | TTTTyTTTC |
| 1 | 850014 | CCTTTTCAC | TCTTGTCACTCTTGTCACTCTTGTCAC | | |
| 1 | 1099971 | GTCGACACC | GTCGACACC | GTCGGCACC | GTCGrCACC |
| 1 | 1350278 | GGAGAGTCG | GGAGAGTCG | GGAGGTTCG | GGAGrkTCG |
| 1 | 1599956 | AATAAGCGC | AATAAGCGC | AATAGGCGC | AATArGCGC |
| 1 | 1850032 | CGAGTAATT | CGAGCAATT | CGAGCAATT | CGAGCAATT |
| 1 | 2119049 | ACAATCCAA | ACAACTCAA | ACAACTCAA | ACAACTCAA |
| 1 | 2400243 | ACTTCATGA | ACTTGATGA | ACTTGATGA | ACTTGATGA |
| 1 | 2612870 | AATAGGAGT | AATAGGAGT | AATAAGAGT | AATArGAGT |
| 1 | 2858975 | GCCGTTCTT | GCCGCTCTTGCCGCTCTTGCCGCTCTT | | |
| 1 | 2804522 | GAAGACGAC | GAAGGCGAC | GAAGGCGAC | GAAGGCGAC |
| 1 | 3047987 | AAGGGGGGG | AAGGAGGGG | AAGGGGGGG | AAGGrGGGG |
| 1 | 3212182 | CACTACGTG | CACTGCGTG | CACTACGTG | CACTrCGTG |
| 1 | 3256057 | TATCTGTTT | TATCCGTTT | TATCCGTTT | TATCCGTTT |
| 2 | 101820 | ATTAAAGAT | ATTAAAGAT | ATTAAAGAT | ATTAAAGAT |
| 2 | 350156 | TCGGGGGTG | TCGGAGGTG | TCGGGGGTG | TCGGrGGTG |
| 2 | 600112 | ATGTATACG | ATGTGTACG | ATGTATACG | ATGTrTACG |
| 2 | 850338 | TGGTGCTAA | TGGTTCTAATGGTGCTAA | TGGTkCTAA | |
| 2 | 1099413 | CCTGACTCA | CCTGGCTCA | CCTGACTCA | CCTGrCTCA |
| 2 | 1349512 | CTCAGCAGT | CTCAACAGT | CTCAGCAGT | CTCArCAGT |
| 2 | 1600085 | CACAATGCC | CACATTGCC | CACAATGCC | CACAwTGCC |
| 2 | 1901773 | ACTCGAATT | ACTAAAATT | ACTCAAATT | ACTmAAATT |
| 2 | 2150201 | GTCGTAGGT | GTCGAAGGT | GTCGTAGGT | GTCGwAGGT |
| 2 | 2400281 | TCAAAACCC | TCAACACCC | TCAACACCC | TCAACACCC |
| 2 | 2650136 | ATAATTCCTATAAGTCCT | ATAATTCCT | ATAAkTCCT | |
| 2 | 2903620 | ACTAAAAGA | ACTAAAAGA | ACTAAAAGA | ACTAAAAGA |
| 2 | 3048019 | GTCCGCTGC | GTCCGCTGC | GTCCGCTGC | GTCCGCTGC |
| 3 | 57117 | TATAGCAGT | TATGACAGT | TATGACAGT | TATGACAGT |
| 3 | 65650 | GGCGCTTTTGGCGGTTTTGGCGGTTTTGGCGGTTTT | | | |
| 3 | 119181 | TTTATACTCTTTATACTCTTTATACTCTTTATACTC | | | |
| 3 | 250112 | GCAGGAGAG | GCCGAAGAG | GCAGGAGAG | GCmGrAGAG |
| 3 | 750000 | GTCCGGCCA | GTCCGGCCA | GTCCGGCCA | GTCCGGCCA |
| 3 | 750074 | AGTTTTTTC | AGTTATTTC | AGTTTTTTC | AGTTwTTTC |
| 3 | 1250000 | TTTTTCCGG | TTTTTCCGG | TTTTTCCGG | TTTTTCCGG |
| 3 | 1250161 | AGTCTCCTT | AGTCCCCTT | AGTCTCCTT | AGTCyCCTT |
| 3 | 1750000 | ACGCCTGAC | ACGCCTGAC | ACGCCTGAC | ACGCCTGAC |
| 3 | 1750033 | TTTTTTGCT | TTTTGTGCT | TTTTTTGCT | TTTTkTGCT |
| 3 | 2250000 | CGTGGCGAT | CGTGGCGAT | CGTGGCGAT | CGTGGCGAT |
| 3 | 2250027 | TGTATCAAG | TGTATCAAG | TGTGCCAAG | TGTryCAAG |
| 3 | 2520748 | TAATTCCAC | TAATGCCAC | TAATTCCAC | TAATkCCAC |
| 4 | 100004 | GAGTGATAA | GAGTGATAA | GAGTGATAA | GAGTGATAA |
| 4 | 490648 | CGATCGCGT | CGATCGCGT | CGATTGCGT | CGATyGCGT |
| 4 | 598147 | GATCGACAG | GATCAACAG | GATCGACAG | GATCrACAG |
| 4 | 852119 | CGAATATTC | CGAATATTC | CGAATATTC | CGAATATTC |
| 4 | 1100085 | GATGCCGAA | GATGACGAA | GATGCCGAA | GATGmCGAA |
| 4 | 1350536 | CGAACTCGG | CGAAATCGG | CGAACTCGG | CGAAmTCGG |
| 4 | 1599885 | GATACTTGC | GATACTTGC | GATACTTGC | GATACTTGC |
| 4 | 1850288 | ATTCGTGTAATTCATGTAATTCGTGTAATTCrTGTA | | | |
| 4 | 2100356 | TCAGAGACC | TCAGAGACC | TCAGGGACC | TCAGrGACC |
| 4 | 2284257 | TCTGGACTG | TCTGAACTG | TCTGAACTG | TCTGrACTG |
| 5 | 100211 | TCCTTGAATTCCTGGAAT | TCCTGGAAT | TCCTGGAAT | |
| 5 | 350872 | GGCGTGCCC | GGCGTGCCC | GGCGTGCCC | GGCGyGCCC |
| 5 | 599922 | CGTCATTCA | CGTCATTCA | CGTCGTTCA | CGTCrTTCA |
| 5 | 851262 | TAATTCTCTTAATCGTCTTAATCGTCTTAATCGTCT | | | |
| 5 | 1099776 | ACATTGACA | ACATTGACA | ACATTGACA | ACATyGACA |
| 5 | 1352539 | TTGTGATCCTTGTGATCCTTGTTGTCCTTGTkrTCC | | | |
| 5 | 1599904 | AACTTCCTT | AACTCCCTT | AACTCCCTT | AACTCCCTT |
| 5 | 1851458 | AAATAATCC | AAATTCTCC | AAATTCTCC | AAATTCTCC |
| 5 | 2100025 | CCCTTAGTCCCCTTAGTCCCCTCAGTC | CCCTyAGTC | | |
| 5 | 2278878 | GGTCAAAAA | GGTCAAAAA | AGTCAAAAA | rGTCAAAAA |

TABLE I-continued

| Scaffold [H97 V2.0 ref. coordinates] | Position of SNP | Cultures: H97 | Wild Line | J14756-s3 | J15051 |
|---|---|---|---|---|---|
| 6 | 106294 | GCCATCTCG | GCCACCTCG | GCCATCTCG | GCCAyCTCG |
| 6 | 350337 | CATTTGGTTC | ATTCGGTTC | ATTTGGTTC | ATTyGGTT |
| 6 | 600047 | GGAGCATTT | GGAGTATTT | GGAGCATTT | GGAGyATTT |
| 6 | 849985 | AGTTCAGGA | AGTTCAGGA | AGTTCAGGA | AGTTCAGGA |
| 6 | 1098535 | CAAAGATTG | CAAAAATTG | CAAAGATTG | CAAArATTG |
| 6 | 1349453 | TGTCGGTAG | TGTCAATAG | TGTCGGTAG | TGTCrrTAG |
| 6 | 1600000 | AAACCTGGA | AAACCTGGA | AAACCTGGA | AAACCTGGA |
| 6 | 1764645 | AACCAGATT | AACCGGATT | AACCGGATT | AACCrGATT |
| 6 | 2000087 | GATTTTGCGG | ATTTTGCGG | ATTTTGCGG | ATTTTGCG |
| 6 | 2252662 | GGGTTGGTA | GGGTCGGTA | GGGTTGGTA | GGGTyGGTA |
| 7 | 100284 | GAAATTCAG | GAAACTCAG | GAAATTCAG | GAAAyTCAG |
| 7 | 350044 | ATATTCTTT | ATATCCTTT | ATATTCTTT | ATATyCTTT |
| 7 | 600111 | CAATTATTACAATCATTA | | CAATTATTA | CAATyATTA |
| 7 | 850246 | TGACGCATA | TGACGCATA | TGACGCATA | TGACGCATA |
| 7 | 1100248 | TCACGGAAG | TCACAGAAG | TCACGGAAG | TCACrGAAG |
| 7 | 1350089 | CTTTTCCCC | CTTTTCCCC | CTTTTCCCC | CTTTTCCCC |
| 7 | 1605047 | ATACTTGGC | ATACTTGAC | ATACTTGGC | ATACTTGrC |
| 7 | 1860993 | GTCAACCGG | GTCATCCGG | GTCAACCGG | GTCAwCCGG |
| 7 | 1898793 | TCCGCATAA | TCCGCATAA | TCCGCATAA | TCCGCATAA |
| 7 | 1991505 | TCTACGGTTTCTACGGTTTCTACGGTTTCTACGGTT | | | |
| 8 | 350000 | ATTGACGCG | ATTGGCGCG | ATTGGCGCG | ATTGGCGCG |
| 8 | 610549 | GAACTTGAT | GAATACGAT | GAATTTGAT | GATwyGAT |
| 8 | 1100000 | CATACGATC | CATACGATC | CATACGATC | CATACGATC |
| 8 | 1100546 | GCCCCAGAA | GCCCCAGAA | GCCCGAGAA | GCCCsAGAA |
| 8 | 1350000 | AGCTTAACA | AGCTTAACA | AGCTTAACA | AGCTTAACA |
| 8 | 1350240 | ACGGGTACT | ACGGATACT | ACGGGTACT | ACGGrTACT |
| 8 | 1600100 | CTGAACCCT | CTGAACCCT | CTGAACCCT | CTGAACCCT |
| 9 | 100105 | CTCAACCGA | CTCAACCGA | CTCAGCCGA | CTCArCCGA |
| 9 | 352455 | AGTCCTCCA | AGTCCTCCA | AGTCTCCCA | AGTCyyCCA |
| 9 | 599950 | TGGTATCCC | TGGTGTCCC | TGGTGTCCC | TGGTGTCCC |
| 9 | 1010845 | GGGTGGTGA | GGGTGGTGA | GGGTAGTGA | GGGTrGTGA |
| 9 | 1244202 | GATGAAGAT | GATGAAGAT | GATGGAGAT | GATGrAGAT |
| 9 | 1504476 | TACTGTACC | TACTGTACC | TACTATACC | TACTrTACC |
| 9 | 1656962 | TATCTACTGTATCTACTGTATCTACTGTATCTACTG | | | |
| 10 | 100438 | AATTAATTTGATTAATTTAATTAATTTrATTAATTT | | | |
| 10 | 350030 | GCGGCTCAA | GCGGTTCAA | GCGGTTCAA | GCGGTTCAA |
| 10 | 600032 | TTACACTGG | TTACACTGG | TTACACTGG | TTACACTGG |
| 10 | 850000 | TCGGTCGGA | TCGGTCGGA | TCGGTCGGA | TCGGTCGGA |
| 10 | 860249 | CCGCAAATT | CCGCGAATT | CCGCAAATT | CCGCrAATT |
| 10 | 1173178 | ATCCCCAAT | ATCCTCAAT | ATCCTCAAT | ATCCTCAAT |
| 10 | 1303902 | TGATTTACTTGATTTACTTGATTTACTTGATTTACT | | | |
| 10 | 1490452 | AATCAGATG | AATCAGATG | AATCAGATG | AATCAGATG |
| 11 | 101855 | CCAGCCTGT | CCAGTCTGT | CCAGCCTGT | CCAGyCTGT |
| 11 | 350000 | GTCAGCAAG | GTCAGCAAG | GTCAGCAAG | GTCAGCAAG |
| 11 | 350025 | GATAAAACA | GATAAAACA | GATATAACA | GATAwAACA |
| 11 | 600000 | ATGGGCGCG | ATGGGAGCG | ATGGGAGCG | ATGGGrGCG |
| 11 | 929659 | GGAATATCA | GGAAGTTCA | GGAATATCA | GGAAkwTCA |
| 11 | 1100608 | AGTGGTCTTAGTGGTCTTAGTGATCTTAGTGrTCTT | | | |
| 11 | 1240230 | ACAAGTTTC | ACAAATTTC | ACAAGTTTC | ACAArTTTC |
| 12 | 100000 | CCTTCTAGTCCTTCTAGTCCTTCTAGTCCTTCTAGT | | | |
| 12 | 109790 | GTCTGCACC | GTCTACACC | GTCTGCACC | GTCTrCACC |
| 12 | 1000000 | CGAGGAGGA | CGAGGAGGA | CGAGAAGGA | CGAGrAGGA |
| 13 | 100697 | ACGTCTTTAACGTCTTTAACGTCTTTAACGTCTTTA | | | |
| 13 | 370521 | TTTGAGTCATTTGTGTCATTTGTGTCATTTGTGTCA | | | |
| 13 | 604345 | CTTCAGCAT | CTTCAGCAT | CTTCAGCAT | CTTCAGCAT |
| 13 | 850249 | GGCTAGTAA | GGCTAGTAA | GGCTAGTAA | GGCTAGTAA |
| 14 | 113109 | AGGGAAATA | AGGGGAATA | AGGGAAATA | AGGGrAATA |
| 14 | 372086 | CGATCCCTTCGATTCCTTCGATCCCTTCGATyCCTT | | | |
| 14 | 725684 | ATGAGTTCG | ATGAGTTTG | ATGAATTCG | ATGArTTyG |
| 15 | 150013 | GTGGCCCGT | GTGGACCGT | GTGGCCCGT | GTGGmCCGT |
| 15 | 449860 | GAATTTCGG | GAATTTCGG | GAATTTCGG | GAATTTCGG |
| 16 | 205778 | CAAGGTCTG | CAAGATCTG | CAAGATCTG | CAAGATCTG |
| 16 | 400000 | CCTCGGATT | CCTCGGATT | CCTCGGATT | CCTCGGATT |
| 16 | 403998 | CCAAGTACG | CCAAATACG | CCAAGTACG | CCAArTACG |

TABLE I-continued

| Scaffold [H97 V2.0 ref. coordinates] | Position of SNP | Cultures: | | | |
|---|---|---|---|---|---|
| | | H97 | Wild Line | J14756-s3 | J15051 |
| 17 | 120000 | TATTCTTCA | TATTCTTCA | TATTCTTCA | TATTCTTCA |
| 17 | 134676 | TTGCCCAGC | TTGCTCAGC | TTGCCCAGC | TTGCyCAGC |
| 17 | 338415 | TGAGAAGCC | TGAGAAGCC | TGAGAAGCC | TGAGAAGCC |
| 17 | 449833 | ATCAGACAA | ATCAAACAA | ATCAAACAA | ATCAAACAA |
| 18 | 101884 | ATTACGGAC | ATTACGGAC | ATTACGGAC | ATTACGGAC |
| 18 | 112940 | GCGGGTGGG | GCGGCTGGG | GCGGGTGGG | GCGGsTGGG |
| 19 | 98520 | GCTATTGGG | GCTATTGGG | GCTATTGGG | GCTATTGGG |
| 19 | 98782 | AAAATTGTT | AAAAGTGTT | AAAATTGTT | AAAAkTGTT | and wherein Table II is provided as follows:

TABLE II

| Strain: | Markers: | | | | | | |
|---|---|---|---|---|---|---|---|
| | p1n150/MatMFPC-1-ELF | FF | AN | AS | ITS | | Match % |
| J15051 | 2/5 | E3/E4 | FF2/FF2 | N3/N4SA | SDI1/I5 | | [100%] |
| B14528 | 2/5 | E3/E4 | FF1/FF3 | N3/N4SC | SDI1/I2 | | 66.7% |
| 28c, [Heirloom] | 1T/5 | E3/E4 | FF1/FF3 | N2/N3SA | SDI1/I1 | | 58.3% |
| 28b, [Braun] | 1T/5 | E3/E4 | FF1/FF4 | N2N3/SB | SDI1/I1 | | 50.0% |
| PTA-6877 | 1T/2 | E2/E3 | FF1/FF1 | N2/N4SD | SDI1/I2 | | 33.3% |
| S600 | 1T/2 | E1/E3 | FF2/FF2 | N2/N4SC | SDI1/I2 | | 41.7% |
| J10263/2 | 1T/2 | E1/E3 | FF2/FF7 | N4/N7SC | SDI1/I2 | | 50.0% |
| OFB$_{lineage\ group}$ | 1T/3 | E3/E6 | FF1/FF2 | N4/N4SC | SDI1/I3 | | 41.7% |
| J14756-s3 | 2 | E3 | FF2 | N4 | SD | I5 | |
| wild line | 5 | E4 | FF2 | N3 | SA | I1, | | from the subsequent hybrid of step (d).

12. The *Agaricus bisporus* culture of claim 2, wherein said F1 hybrid mushroom culture is a culture of strain J15051, a culture of the strain J15051 having been deposited under the NRRL accession number 67316.

13. The *Agaricus bisporus* culture of claim 2, wherein said F1 hybrid mushroom culture produces, when grown under the same commercial conditions with at least one dark-brown strain selected from the group consisting of BR06/"Heirloom" and B14528/"Tuscan," a crop of mushrooms (1) having a cap color that is a lighter brown color than at least one of the dark-brown strains selected from the group, and wherein (2) the crop is produced not later than crops produced by at least one of the dark-brown strains selected from the group, and wherein (3) the crop yield is at least 95% of the yield of at least one of the dark-brown strains selected from the group.

14. An Essentially Derived Variety culture from an initial culture which is the culture of claim 12, wherein the Essentially Derived Variety culture has at least 75% genotypic and genomic identity with the culture of strain J15051.

15. A part of the culture of claim 2 selected from the group consisting of hyphae and cells.

16. A part of the culture of claim 12 selected from the group consisting of hyphae, spores, cells, and nuclei.

17. A mushroom produced by growing a crop of mushrooms from the culture of claim 1.

18. A mushroom produced by growing a crop of mushrooms from the F1 hybrid *Agaricus bisporus* mushroom culture of claim 2.

19. A process of producing a hybrid mushroom culture, comprising:

physically mating a first *Agaricus bisporus* mushroom culture with a second *Agaricus bisporus* mushroom culture, wherein at least one of the first and second mushroom cultures is a culture having all of the physiological and morphological characteristics of line J14756-s3, wherein a culture of said line J14756-s3 having been deposited under the NRRL Accession Number 67317.

20. A hybrid culture produced by the process of claim 19.

21. A part of the hybrid culture of claim 20, selected from the group consisting of hyphae and cells.

22. A hybrid mushroom, or its pieces or parts, produced by growing a crop of mushrooms from said hybrid culture of claim 20.

23. A product incorporating the hybrid culture of claim 20, the product selected from the group consisting of mycelium, spawn, inoculum, casing inoculum, fresh mushrooms, processed mushrooms, mushroom pieces, colonized substrates, grain, compost, and friable particulate matter.

24. A method of mushroom strain development comprising the steps of:
(a) obtaining a molecular marker profile of *Agaricus bisporus* mushroom line J14756-s3, a culture of said line having been deposited under the NRRL Accession Number 67317;
(b) obtaining an $F_n$ hybrid culture for which the mushroom culture of claim 1 is a parent, wherein n is an integer 1 to 10;
(c) mating a culture obtained from the $F_n$ hybrid culture with a different mushroom culture to produce an $F_{(n+1)}$ hybrid culture; and
(d) selecting progeny of the $F_{(n+1)}$ hybrid culture that possess characteristics of said molecular marker profile of line J14756-s3.

25. An *Agaricus bisporus* culture having all of the physiological and morphological characteristics of line J14756-s3, wherein a culture of said line J14756-s3 having been deposited under the NRRL Accession Number 67317.

26. The *Agaricus bisporus* culture of claim 25, further comprising a marker profile in accordance with the marker profile of line J14756-s3 shown in Table I, wherein Table is provided as follows:

TABLE I

| Scaffold | Position of SNP | Cultures: | | | |
|---|---|---|---|---|---|
| [H97 V2.0 ref. coordinates] | | H97 | Wild Line | J14756-s3 | J15051 |
| 1 | 99995 | CTACATTGA | CTACGTTGA | CTACGTTGA | CTACGTTGA |
| 1 | 349966 | AAGGTGGTT | AAGGCGGTT | AAGGCGGTT | AAGGCGGTT |
| 1 | 600059 | TTTTTTTT- | TTTTTTTTC | TTTTCTTT- | TTTTyTTTC |
| 1 | 850014 | CCTTTTCAC | TCTTGTCAC | TCTTGTCAC | TCTTGTCAC |
| 1 | 1099971 | GTCGACACC | GTCGACACC | GTCGGCACC | GTCGrCACC |
| 1 | 1350278 | GGAGAGTCG | GGAGAGTCG | GGAGGTTCG | GGAGrkTCG |
| 1 | 1599956 | AATAAGCGC | AATAAGCGC | AATAGGCGC | AATArGCGC |
| 1 | 1850032 | CGAGTAATT | CGAGCAATT | CGAGCAATT | CGAGCAATT |
| 1 | 2119049 | ACAATCCAA | ACAACTCAA | ACAACTCAA | ACAACTCAA |
| 1 | 2400243 | ACTTCATGA | ACTTGATGA | ACTTGATGA | ACTTGATGA |
| 1 | 2612870 | AATAGGAGT | AATAGGAGT | AATAAGAGT | AATArGAGT |
| 1 | 2858975 | GCCGTTCTT | GCCGCTCTT | GCCGCTCTT | GCCGCTCTT |
| 1 | 2804522 | GAAGACGAC | GAAGGCGAC | GAAGGCGAC | GAAGGCGAC |
| 1 | 3047987 | AAGGGGGGG | AAGGAGGGG | AAGGGGGGG | AAGGrGGGG |
| 1 | 3212182 | CACTACGTG | CACTGCGTG | CACTACGTG | CACTrCGTG |
| 1 | 3256057 | TATCTGTTT | TATCCGTTT | TATCCGTTT | TATCCGTTT |
| 2 | 101820 | ATTAAAGAT | ATTAAAGAT | ATTAAAGAT | ATTAAAGAT |
| 2 | 350156 | TCGGGGGTG | TCGGAGGTG | TCGGGGGTG | TCGGrGGTG |
| 2 | 600112 | ATGTATACG | ATGTGTACG | ATGTATACG | ATGTrTACG |
| 2 | 850338 | TGGTGCTAA | TGGTTCTAA | TGGTGCTAA | TGGTkCTAA |
| 2 | 1099413 | CCTGACTCA | CCTGGCTCA | CCTGACTCA | CCTGrCTCA |
| 2 | 1349512 | CTCAGCAGT | CTCAACAGT | CTCAGCAGT | CTCArCAGT |
| 2 | 1600085 | CACAATGCC | CACATTGCC | CACAATGCC | CACAwTGCC |
| 2 | 1901773 | ACTCGAATT | ACTAAAATT | ACTCAAATT | ACTmAAATT |
| 2 | 2150201 | GTCGTAGGT | GTCGAAGGT | GTCGTAGGT | GTCGwAGGT |
| 2 | 2400281 | TCAAAACCC | TCAACACCC | TCAACACCC | TCAACACCC |
| 2 | 2650136 | ATAATTCCTATAAGTCCT | | ATAATTCCT | ATAAkTCCT |
| 2 | 2903620 | ACTAAAAGA | ACTAAAAGA | ACTAAAAGA | ACTAAAAGA |
| 2 | 3048019 | GTCCGCTGC | GTCCGCTGC | GTCCGCTGC | GTCCGCTGC |
| 3 | 57117 | TATAGCAGT | TATGACAGT | TATGACAGT | TATGACAGT |
| 3 | 65650 | GGCGCTTTTGGCGGTTTTGGCGGTTTTGGCGGTTTT | | | |
| 3 | 119181 | TTTATACTCTTTATACTCTTTATACTCTTTATACTC | | | |
| 3 | 250112 | GCAGGAGAG | GCCGAAGAG | GCAGGAGAG | GCmGrAGAG |
| 3 | 750000 | GTCCGGCCA | GTCCGGCCA | GTCCGGCCA | GTCCGGCCA |
| 3 | 750074 | AGTTTTTTC | AGTTATTTC | AGTTTTTTC | AGTTwTTTC |
| 3 | 1250000 | TTTTTCCGG | TTTTTCCGG | TTTTTCCGG | TTTTTCCGG |
| 3 | 1250161 | AGTCTCCTT | AGTCCCCTT | AGTCTCCTT | AGTCyCCTT |
| 3 | 1750000 | ACGCCTGAC | ACGCCTGAC | ACGCCTGAC | ACGCCTGAC |
| 3 | 1750033 | TTTTTTGCT | TTTTGTGCT | TTTTTTGCT | TTTTkTGCT |
| 3 | 2250000 | CGTGGCGAT | CGTGGCGAT | CGTGGCGAT | CGTGGCGAT |
| 3 | 2250027 | TGTATCAAG | TGTGCCAAG | TGTATCAAG | TGTryCAAG |
| 3 | 2520748 | TAATTCCAC | TAATGCCAC | TAATTCCAC | TAATkCCAC |
| 4 | 100004 | GAGTGATAA | GAGTGATAA | GAGTGATAA | GAGTGATAA |
| 4 | 490648 | CGATCGCGT | CGATTGCGT | CGATCGCGT | CGATyGCGT |
| 4 | 598147 | GATCGACAG | GATCAACAG | GATCGACAG | GATCrACAG |
| 4 | 852119 | CGAATATTC | CGAATATTC | CGAATATTC | CGAATATTC |
| 4 | 1100085 | GATGCCGAA | GATGACGAA | GATGCCGAA | GATGmCGAA |
| 4 | 1350536 | CGAACTCGG | CGAAATCGG | CGAACTCGG | CGAAmTCGG |
| 4 | 1599885 | GATACTTGC | GATACTTGC | GATACTTGC | GATACTTGC |
| 4 | 1850288 | ATTCGTGTAATTCATGTAATTCGTGTAATTCrTGTA | | | |
| 4 | 2100356 | TCAGAGACC | TCAGAGACC | TCAGGGACC | TCAGrGACC |
| 4 | 2284257 | TCTGGACTG | TCTGAACTG | TCTGAACTG | TCTGrACTG |
| 5 | 100211 | TCCTTGAATTCCTGGAAT | | TCCTGGAAT | TCCTGGAAT |
| 5 | 350872 | GGCGTGCCC | GGCGTGCCC | GGCGCGCCC | GGCGyGCCC |
| 5 | 599922 | CGTCATTCA | CGTCATTCA | CGTCGTTCA | CGTCrTTCA |
| 5 | 851262 | TAATTCTCTTAATCGTCTTAATCGTCTTAATCGTCT | | | |

TABLE I-continued

| Scaffold [H97 V2.0 ref. coordinates] | Position of SNP | Cultures: H97 | Wild Line | J14756-s3 | J15051 |
|---|---|---|---|---|---|
| 5 | 1099776 | ACATTGACA | ACATCGACA | ACATTGACA | ACATyGACA |
| 5 | 1352539 | TTGTGATCCTTGTGATCCTTGTTGTCCTTGTkrTCC | | | |
| 5 | 1599904 | AACTTCCTT | AACTCCCTT | AACTCCCTT | AACTCCCTT |
| 5 | 1851458 | AAATAATCC | AAATTCTCC | AAATTCTCC | AAATTCTCC |
| 5 | 2100025 | CCCTTAGTCCCCTTAGTCCCCTCAGTC | | | CCCTyAGTC |
| 5 | 2278878 | GGTCAAAAA | GGTCAAAAA | AGTCAAAAA | rGTCAAAAA |
| 6 | 106294 | GCCATCTCG | GCCACCTCG | GCCATCTCG | GCCAyCTCG |
| 6 | 350337 | CATTTGGTTCATTCGGTTCATTTGGTTCATTyGGTT | | | |
| 6 | 600047 | GGAGCATTT | GGAGTATTT | GGAGCATTT | GGAGyATTT |
| 6 | 849985 | AGTTCAGGA | AGTTCAGGA | AGTTCAGGA | AGTTCAGGA |
| 6 | 1098535 | CAAAGATTG | CAAAAATTG | CAAAGATTG | CAAArATTG |
| 6 | 1349453 | TGTCGGTAG | TGTCAATAG | TGTCGGTAG | TGTCrrTAG |
| 6 | 1600000 | AAACCTGGA | AAACCTGGA | AAACCTGGA | AAACCTGGA |
| 6 | 1764645 | AACCAGATT | AACCGGATT | AACCGGATT | AACCrGATT |
| 6 | 2000087 | GATTTTGCGGATTTTGCGGATTTTGCGGATTTTGCG | | | |
| 6 | 2252662 | GGGTTGGTA | GGGTCGGTA | GGGTTGGTA | GGGTyGGTA |
| 7 | 100284 | GAAATTCAG | GAAACTCAG | GAAATTCAG | GAAAyTCAG |
| 7 | 350044 | ATATTCTTT | ATATCCTTT | ATATTCTTT | ATATyCTTT |
| 7 | 600111 | CAATTATTACAATCATTA | | CAATTATTA | CAATyATTA |
| 7 | 850246 | TGACGCATA | TGACGCATA | TGACGCATA | TGACGCATA |
| 7 | 1100248 | TCACGGAAG | TCACAGAAG | TCACGGAAG | TCACrGAAG |
| 7 | 1350089 | CTTTTCCCC | CTTTTCCCC | CTTTTCCCC | CTTTTCCCC |
| 7 | 1605047 | ATACTTGGC | ATACTTGAC | ATACTTGGC | ATACTTGrC |
| 7 | 1860993 | GTCAACCGG | GTCATCCGG | GTCAACCGG | GTCAwCCGG |
| 7 | 1898793 | TCCGCATAA | TCCGCATAA | TCCGCATAA | TCCGCATAA |
| 7 | 1991505 | TCTACGGTTTCTACGGTTTCTACGGTTTCTACGGTT | | | |
| 8 | 350000 | ATTGACGCG | ATTGGCGCG | ATTGGCGCG | ATTGGCGCG |
| 8 | 610549 | GAACTTGAT | GAATACGAT | GAATTTGAT | GATwyGAT |
| 8 | 1100000 | CATACGATC | CATACGATC | CATACGATC | CATACGATC |
| 8 | 1100546 | GCCCCAGAA | GCCCCAGAA | GCCCGAGAA | GCCCsAGAA |
| 8 | 1350000 | AGCTTAACA | AGCTTAACA | AGCTTAACA | AGCTTAACA |
| 8 | 1350240 | ACGGGTACT | ACGGATACT | ACGGGTACT | ACGGrTACT |
| 8 | 1600100 | CTGAACCCT | CTGAACCCT | CTGAACCCT | CTGAACCCT |
| 9 | 100105 | CTCAACCGA | CTCAACCGA | CTCAGCCGA | CTCArCCGA |
| 9 | 352455 | AGTCCTCCA | AGTCCTCCA | AGTCTCCCA | AGTCyyCCA |
| 9 | 599950 | TGGTATCCC | TGGTGTCCC | TGGTGTCCC | TGGTGTCCC |
| 9 | 1010845 | GGGTGGTGA | GGGTGGTGA | GGGTAGTGA | GGGTrGTGA |
| 9 | 1244202 | GATGAAGAT | GATGAAGAT | GATGGAGAT | GATGrAGAT |
| 9 | 1504476 | TACTGTACC | TACTGTACC | TACTATACC | TACTrTACC |
| 9 | 1656962 | TATCTACTGTATCTACTGTATCTACTGTATCTACTG | | | |
| 10 | 100438 | AATTAATTTGATTAATTTAATTAATTTrATTAATTT | | | |
| 10 | 350030 | GCGGCTCAA | GCGGTTCAA | GCGGTTCAA | GCGGTTCAA |
| 10 | 600032 | TTACACTGG | TTACACTGG | TTACACTGG | TTACACTGG |
| 10 | 850000 | TCGGTCGGA | TCGGTCGGA | TCGGTCGGA | TCGGTCGGA |
| 10 | 860249 | CCGCAAATT | CCGCGAATT | CCGCAAATT | CCGCrAATT |
| 10 | 1173178 | ATCCCCAAT | ATCCTCAAT | ATCCTCAAT | ATCCTCAAT |
| 10 | 1303902 | TGATTTACTTGATTTACTTGATTTACTTGATTTACT | | | |
| 10 | 1490452 | AATCAGATG | AATCAGATG | AATCAGATG | AATCAGATG |
| 11 | 101855 | CCAGCCTGT | CCAGTCTGT | CCAGCCTGT | CCAGyCTGT |
| 11 | 350000 | GTCAGCAAG | GTCAGCAAG | GTCAGCAAG | GTCAGCAAG |
| 11 | 350025 | GATAAAACA | GATAAAACA | GATATAACA | GATAwAACA |
| 11 | 600000 | ATGGGCGCG | ATGGGAGCG | ATGGGAGCG | ATGGGrGCG |
| 11 | 929659 | GGAATATCA | GGAAGTTCA | GGAATATCA | GGAAkwTCA |
| 11 | 1100608 | AGTGGTCTTAGTGGTCTTAGTGATCTTAGTGrTCTT | | | |
| 11 | 1240230 | ACAAGTTTC | ACAAATTTC | ACAAGTTTC | ACAArTTTC |
| 12 | 100000 | CCTTCTAGTCCTTCTAGTCCTTCTAGTCCTTCTAGT | | | |
| 12 | 109790 | GTCTGCACC | GTCTACACC | GTCTGCACC | GTCTrCACC |
| 12 | 1000000 | CGAGGAGGA | CGAGGAGGA | CGAGAAGGA | CGAGrAGGA |
| 13 | 100697 | ACGTCTTTAACGTCTTTAACGTCTTTAACGTCTTTA | | | |
| 13 | 370521 | TTTGAGTCATTTGTGTCATTTGTGTCATTTGTGTCA | | | |
| 13 | 604345 | CTTCAGCAT | CTTCAGCAT | CTTCAGCAT | CTTCAGCAT |
| 13 | 850249 | GGCTAGTAA | GGCTAGTAA | GGCTAGTAA | GGCTAGTAA |
| 14 | 113109 | AGGGAAATA | AGGGGAATA | AGGGAAATA | AGGGrAATA |
| 14 | 372086 | CGATCCCTTCGATTCCTTCGATCCCTTCGATyCCTT | | | |
| 14 | 725684 | ATGAGTTCG | ATGAGTTTG | ATGAATTCG | ATGArTTyG |

TABLE I-continued

| Scaffold [H97 V2.0 ref. coordinates] | Position of SNP | Cultures: H97 | Wild Line | J14756-s3 | J15051 |
|---|---|---|---|---|---|
| 15 | 150013 | GTGGCCCGT | GTGGACCGT | GTGGCCCGT | GTGGmCCGT |
| 15 | 449860 | GAATTTCGG | GAATTTCGG | GAATTTCGG | GAATTTCGG |
| 16 | 205778 | CAAGGTCTG | CAAGATCTG | CAAGATCTG | CAAGATCTG |
| 16 | 400000 | CCTCGGATT | CCTCGGATT | CCTCGGATT | CCTCGGATT |
| 16 | 403998 | CCAAGTACG | CCAAATACG | CCAAGTACG | CCAArTACG |
| 17 | 120000 | TATTCTTCA | TATTCTTCA | TATTCTTCA | TATTCTTCA |
| 17 | 134676 | TTGCCCAGC | TTGCTCAGC | TTGCCCAGC | TTGCyCAGC |
| 17 | 338415 | TGAGAAGCC | TGAGAAGCC | TGAGAAGCC | TGAGAAGCC |
| 17 | 449833 | ATCAGACAA | ATCAAACAA | ATCAAACAA | ATCAAACAA |
| 18 | 101884 | ATTACGGAC | ATTACGGAC | ATTACGGAC | ATTACGGAC |
| 18 | 112940 | GCGGGTGGG | GCGGCTGGG | GCGGGTGGG | GCGGsTGGG |
| 19 | 98520 | GCTATTGGG | GCTATTGGG | GCTATTGGG | GCTATTGGG |
| 19 | 98782 | AAAATTGTT | AAAAGTGTT | AAAATTGTT | AAAAkTGTT. |

27. An Essentially Derived Variety culture derived from an initial culture which is the culture of claim 2, wherein the Essentially Derived Variety culture has at least 75% genotypic and genomic identity with the culture of the F1 hybrid mushroom culture produced by mating a culture of the line J14756-s3 with a different *Agaricus bisporus* culture.

* * * * *

SEQUENCE LISTING

```
<160> NUMBER OF SEQ ID NOS: 12

<210> SEQ ID NO 1
<211> LENGTH: 18
<212> TYPE: DNA
<213> ORGANISM: Agaricus bisporus

<400> SEQUENCE: 1
aggcryccca tcttcasc                                                       18

<210> SEQ ID NO 2
<211> LENGTH: 17
<212> TYPE: DNA
<213> ORGANISM: Agaricus bisporus

<400> SEQUENCE: 2
gttcgacgac ggactgc                                                        17

<210> SEQ ID NO 3
<211> LENGTH: 19
<212> TYPE: DNA
<213> ORGANISM: Agaricus bisporus

<400> SEQUENCE: 3
tccgtaggtg aaccggcgg                                                      19

<210> SEQ ID NO 4
<211> LENGTH: 20
<212> TYPE: DNA
<213> ORGANISM: Agaricus bisporus

<400> SEQUENCE: 4
tcctccgctt attgatatgc                                                     20

<210> SEQ ID NO 5
<211> LENGTH: 23
<212> TYPE: DNA
<213> ORGANISM: Agaricus bisporus
```

```
<400> SEQUENCE: 5
aytcrcaama acataccttc aac                                        23

<210> SEQ ID NO 6
<211> LENGTH: 18
<212> TYPE: DNA
<213> ORGANISM: Agaricus bisporus

<400> SEQUENCE: 6
cattcggcga ttttctca                                              18

<210> SEQ ID NO 7
<211> LENGTH: 21
<212> TYPE: DNA
<213> ORGANISM: Agaricus bisporus

<400> SEQUENCE: 7
gacgatgcgg gactggtgga t                                          21

<210> SEQ ID NO 8
<211> LENGTH: 23
<212> TYPE: DNA
<213> ORGANISM: Agaricus bisporus

<400> SEQUENCE: 8
ggtctggcct acrggagtgt tgt                                        23

<210> SEQ ID NO 9
<211> LENGTH: 23
<212> TYPE: DNA
<213> ORGANISM: Agaricus bisporus

<400> SEQUENCE: 9
ccgccagcac aaggaatcaa atg                                        23

<210> SEQ ID NO 10
<211> LENGTH: 23
<212> TYPE: DNA
<213> ORGANISM: Agaricus bisporus

<400> SEQUENCE: 10
tcagtcggcc ctcaaaacag tcg                                        23

<210> SEQ ID NO 11
<211> LENGTH: 22
<212> TYPE: DNA
<213> ORGANISM: Agaricus bisporus

<400> SEQUENCE: 11
tcgggtggtt gcaactgaaa ag                                         22

<210> SEQ ID NO 12
<211> LENGTH: 24
<212> TYPE: DNA
<213> ORGANISM: Agaricus bisporus

<400> SEQUENCE: 12
ttcctttccg ccttaattgt ttct                                       24
```